(12) United States Patent
Mace et al.

(10) Patent No.: US 10,758,846 B2
(45) Date of Patent: Sep. 1, 2020

(54) SEPARATION OF CELLS BASED ON SIZE AND AFFINITY USING PAPER MICROFLUIDIC DEVICE

(71) Applicant: Trustees of Tufts College, Medford, MA (US)

(72) Inventors: Charles R. Mace, Watertown, MA (US); Syrena C. Fernandes, Somerville, MA (US); Samuel B. Berry, Orangeburg, NY (US)

(73) Assignee: Trustees of Tufts College, Medford, MA (US)

( * ) Notice: Subject to any disclaimer, the term of this patent is extended or adjusted under 35 U.S.C. 154(b) by 223 days.

(21) Appl. No.: 16/033,261

(22) Filed: Jul. 12, 2018

(65) Prior Publication Data
US 2018/0318732 A1 Nov. 8, 2018

Related U.S. Application Data

(63) Continuation-in-part of application No. PCT/US2017/013065, filed on Jan. 11, 2017.
(Continued)

(51) Int. Cl.
*B01D 29/01* (2006.01)
*B01D 39/18* (2006.01)
(Continued)

(52) U.S. Cl.
CPC .......... *B01D 29/01* (2013.01); *B01D 29/58* (2013.01); *B01D 39/18* (2013.01); *G01N 33/491* (2013.01);
(Continued)

(58) Field of Classification Search
CPC ........ B01D 29/01; B01D 29/58; B01D 39/18; G01N 31/22; G01N 33/491; G01N 33/57415
See application file for complete search history.

(56) References Cited

U.S. PATENT DOCUMENTS 5,087,556 A 2/1992 Ertinghausen
7,115,421 B2 10/2006 Grzeda
(Continued)

OTHER PUBLICATIONS

Ahlstrom Laboratory Products Catalog, available at http://www.ahlstrom.com/globalassets/files/medical-care-and-life-science-files/ahlstrom-laboratory-catalogue-en.pdf, accessed on Jul. 19, 2015 (20 pages).
(Continued)

*Primary Examiner* — Jennifer Wecker
(74) *Attorney, Agent, or Firm* — Nixon Peabody LLP

(57) ABSTRACT

A microfluidic device includes a first layer of a porous material with pores having a first average pore size and a liquid-receiving area through which a liquid sample is received into the microfluidic device. A second layer of another porous material, with pores of a second average pore size, is stacked below the first layer and has a channel with a starting end positioned at least in part in an overlapping manner with the liquid-receiving area. The channel has a terminating end extending laterally at a predetermined wicking distance from the starting end. The first average pore size and the second average pore size cause a wicking effect in which at least some of the liquid sample flows along the channel at least a portion of the wicking distance between the starting end and the terminating end.

6 Claims, 25 Drawing Sheets

Related U.S. Application Data

(60) Provisional application No. 62/277,810, filed on Jan. 12, 2016.

(51) Int. Cl.
  G01N 33/49 (2006.01)
  B01D 29/58 (2006.01)
  G01N 33/574 (2006.01)
  G01N 31/22 (2006.01)

(52) U.S. Cl.
  CPC ....... G01N 33/57415 (2013.01); G01N 31/22 (2013.01)

(56) References Cited

U.S. PATENT DOCUMENTS

| | | |
|---|---|---|
| 2008/0038759 A1 | 2/2008 | Keren |
| 2010/0267065 A1 | 10/2010 | Geiger |
| 2011/0111517 A1 | 5/2011 | Siegel |
| 2012/0217159 A1* | 8/2012 | Bar-Or ................... G01N 33/49 204/403.02 |
| 2012/0322086 A1 | 12/2012 | Garnier |
| 2013/0267005 A1 | 10/2013 | Kartalov |
| 2013/0331666 A1 | 12/2013 | Miller |
| 2014/0065647 A1 | 3/2014 | Mamenta |
| 2014/0295415 A1* | 10/2014 | Rolland ..................... B01L 7/52 435/6.1 |
| 2014/0295472 A1 | 10/2014 | Shevkoplyas |
| 2015/0266023 A1 | 9/2015 | Fuchiwaki |

OTHER PUBLICATIONS

Amundsen, E.K. et al., "Absolute Neutrophil Counts From Automated Hematology Instruments are Accurate and Precise Even at Very Low Levels," Am. J. Clin. Pathol., 2012, vol. 137, pp. 862-869 (8 pages).
Antiretroviral therapy for HIV infection in adults and adolescents: recommendations for a public health approach, Geneva: World Health Organization, 2006, available at http://www.who.int.hiv/pub/guidelines/artadultguidelines.pdf, accessed on Jul. 16, 2015 (134 pages).
Badu-Tawiah, A.K. et al., "Polymerization-based Signal Amplification for Paper-Based Immunoassays," Lab Chip, 2015, vol. 15, pp. 655-659 (5 pages).
Bradley, A.J., "Bovine Mastitis: An Evolving Disease" Vet. J., 2002, vol. 164, pp. 116-128 (13 pages).
Burke, D.F. et al., "A Recommended Numbering Scheme for Influenza A HA Subtypes," PLoS One, Nov. 2014, vol. 9, Issue 11, e112302, pp. 1-6 (6 pages).
Carrilho, E. et al., "Understanding Wax Printing: A Simple Micropatterning Process for Paper-Based Microfluidics," Anal. Chem., 2009, vol. 81, pp. 7091-7095 (5 pages).
Chaplin, H. Jr. et al., "The Body/Venous Hematocrit Ratio: Its Constancy Over a Wide Hematocrit Range," J. Clin. Invest., 1953, vol. 32, pp. 1309-1310 (8 pages).
Cheng, C.-M. et al., "Paper-Based ELISA," Angew. Chem. Int. Ed., 2010, vol. 49, pp. 4771-4774 (4 pages).
Cheng, X. et al., "A Microfluidic Device for Practical Label-Free CD4+ T Cell Counting of HIV-Infected Subjects," Lab Chip, 2007, vol. 7, pp. 170-178 (9 pages).
Chin, C.D. et al., "Microfluidics-Based Diagnostics Diseases in the Developing World," Nat. Med., Aug. 2011, vol. 17, No. 8, pp. 1015-1019 (6 pages).
Clohisy, D.R. et al., "1,25-Dihydroxyvitamin D3 Modulates Bone Marrow Macrophage Precursor Proliferation and Differentiation," J. Biol. Chem., Nov. 25, 1987, vol. 262, No. 33, pp. 15922-15929 (8 pages).
Connelly, J.T. et al., "'Paper Machine' for Molecular Diagnostics," Anal. Chem., 2015, vol. 87, pp. 7595-7601 (7 pages).

Depoil, D. et al., "CD19 is Essential for B Cell Activation by Promoting B Cell Receptor-Antigen Microcluster Formation in Response to Membrane-bound Ligand," Nat. Immunol., Jan. 2008, vol. 9, No. 1, pp. 63-72 (10 pages).
Derda, R. et al., "Paper-Supported 3D Cell Culture for Tissue-Based Bioassays," Proc. Natl. Acad. Sci. USA, 2009, vol. 106, No. 44, pp. 18457-18462 (6 pages).
Derda, R. et al., "Multizone Paper Platform for 3D Cell Cultures," PLoS One, May 2011, vol. 6, Issue 5, e18940, pp. 1-14 (14 pages).
"Diagnostics for All," 2018, available at http://dfa.org/ (3 pages).
Dill, D.B. et al., "Calculation of Percentage Changes in Volumes of Blood, Plasma, and Red Cells in Dehydration," J. Appl. Physiol., Aug. 1974, vol. 37, No. 2, pp. 247-248 (2 pages).
Dungchai, W. et al., "Electrochemical Detection for Paper-Based Microfluidics," Anal. Chem., 2009, vol. 81, pp. 5821-5826 (6 pages).
Dungchai, W. et al., "Use of Multiple Calorimetric Indicators for Paper-Based Microfluidic Devices." Anal. Chim. Acta, 2010, vol. 674, pp. 227-233 (7 pages).
Dunne, J.R. et al., "Perioperative Anemia: An Independent Risk Factor for Infection, Mortality, and Resource Utilization in Surgery," J. Surg. Res., 2002, vol. 102, pp. 237-244.
Ellerbee, A.K. et al., "Quantifying Colorimetric Assays in Paper-Based Microfluidic Devices by Measuring the Transmission of Light Through Paper," Anal. Chem., 2009, vol. 81, pp. 8447-8452 (6 pages).
Epstein, L.B. et al., "Fluorescence-Activated Cell Sorting of Human T and B Lymphocytes: II. Identification of the Cell Type Responsible for Interferon Production and Cell Proliferation in Response to Mitogens," Cell. Immunol., 1974, vol. 12, pp. 407-421 (15 pages).
Fakanya, W.M. et al., "Detection of the Inflammation Biomarker C-Reactive Protein in Serum Samples: Towards an Optimal Biosensor Formula," Biosensors, 2014, vol. 4, pp. 340-357 (18 pages).
Fernandes, S.C. et al., "Comparison of Three Indirect Immunoassay Formats on a Common Paper-Based Microfluidic Device Architecture," Anal. Methods, 2016, vol. 8, pp. 5204-5211 (8 pages).
Flehmig, B. et al., "Hepatitis A Virus in Cell Culture," Med. Microbiol. Immunol., 1981, vol. 170, pp. 73-89 (7 pages).
Floyd, H. et al., "Siglec-8. A Novel Eosinophil-Specific Member of the Immunoglobulin Superfamily." J. Biol. Chem., Jan. 14, 2000, vol. 275, No. 2, pp. 861-866 (7 pages).
Fu, E. et al., "Controlled Reagent Transport in 2D Paper Networks," Lab Chip, Apr. 7, 2010, vol. 10(7), pp. 918-920 (9 pages).
Funes-Huacca, M. et al., "Portable Self-Contained Cultures for Phage and Bacteria Made of Paper and Tape," Lab Chip, 2012, vol. 12, pp. 4269-4278 (10 pages).
Ge, L. et al., "3D Origami-Based Multifunction-Integrated Immunodevice: Low-Cost and Multiplexed Sandwich Chemiluminescence Immunoassay on Microfluidic Paper-Based Analytical Device," Lab Chip, 2012, vol. 12, pp. 3150-3158 (9 pages).
Gill, J.E. et al., "A Rapid and Accurate Closed-tube Immunoassay for Platelets on an Automated Hematology Analyzer," Am. J. Clin. Pathol., 2000, vol. 114, pp. 47-56 (10 pages).
Gohring, K. et al., "Neutrophil CD177 (NB1 gp, HNA-2a) Expression is Increased in Severe Bacterial Infections and Polycythaemia Vera," Brit. J. Haematol., 2004, vol. 126, pp. 252-254 (3 pages).
Glavan, A.C. et al., "Omniphobic '$R^F$ Paper' Produced by Silanization of Paper with Fluoroalkyltrichlorosilanes." Adv. Funct. Mater., 2014, vol. 24, pp. 60-70 (11 pages).
Gossett, D.R. et al., "Label-Free Cell Separation and Sorting in Microfluidic Systems," Anal. Bioanal. Chem., 2010, vol. 397, pp. 3249-3267 (19 pages).
Govindarajan, A.V. et al., "A Low Cost Point-of-Care Viscous Sample Preparation Device for Molecular Diagnosis in the Developing World: An Example of Microfluidic Origami," Lab Chip 2012, vol. 12, pp. 174-181 (8 pages).
Gram, L. et al., "Food Spoilage—Interactions Between Food Spoilage Bacteria," Int. J. Food Microbiol., 2002, vol. 78, pp. 79-97 (19 pages).
Gribble, C.M. et al., "Porometry, Porosimetry, Image Analysis and Void Network Modeling in the Study of the Pore-Level Properties of Filters," Chem. Eng. Sci., 2011, vol. 66, pp. 3701-3709 (9 pages).

(56) References Cited

OTHER PUBLICATIONS

Gubler, D.J. "Resurgent Vector-Borne Diseases as a Global Health Problem," Emerg. Infect. Dis., Jul.-Sep. 1998, vol. 4, No. 3, pp. 442-450 (9 pages).
Jena, A.K. et al., "In-Plane Compression Porometry of Battery Separators," J. Power Sources, 1999, vol. 80, pp. 46-52 (7 pages).
Khan, M.S. et al., "Paper Diagnostic for Instantaneous Blood Typing," Anal. Chem., 2010, vol. 82, pp. 4158-4164 (7 pages).
Klasner, S.A. et al., "Paper-Based Microfluidic Devices for Analysis of Clinically Relevant Analytes Present in Urine and Saliva," Anal. Bioanal. Chem., 2010, vol. 397, pp. 1821-1829 (9 pages).
Kumar, A.A. et al., "Density-Based Separation in Multiphase Systems Provides a Simple Method to Identify Sickle Cell Disease," Proc. Natl. Acad. Sci. USA, Oct. 14, 2014, vol. 111, No. 41, pp. 14864-14869 (6 pages).
Lehrer, R.I. "Neutrophils and Host Defense," Ann. Intern. Med., Jul. 15, 1988, vol. 109, pp. 127-142 (18 pages).
Lewis, G.G. et al., "High Throughput Method for Prototyping Three-Dimensional, Paper-Based Microfluidic Devices," Lab Chip, 2012, vol. 12, pp. 2630-2633 (4 pages).
Li, X. et al., "Progress in Patterned Paper Sizing for Fabrication of Paper-Based Microfluidic Sensors," Cellulose, 2010, vol. 17, pp. 649-659 (11 pages).
Li, X. et al., "A Perspective on Paper-Based Microfluidics: Current Status and Future Trends," Biomicrofluidics, 2012, vol. 6, pp. 011301-1-011301-13 (13 pages).
Liu, H. et al., "Three-Dimensional Paper Microfluidic Devices Assembled Using the Principles of Origami," J. Am. Chem. Soc., 2011, vol. 133, pp. 17564-17566 (3 pages).
Lorenz, H.-M. et al., "The Cell and Molecular Basis of Leukocyte Common Antigen (CD45)-Triggered, Lymphocyte Function-Associated Antigen-1-/Intercellular Adhesion Molecular-1-Dependent, Leukocyte Adhesion," Blood, Apr. 1, 1994, vol. 83, No. 7, pp. 1862-1870 (10 pages).
Mace, C.R. et al., "Aqueous Multiphase Systems of Polymers and Surfactants Provide Self-Assembling Step-Gradients in Density," J. Am. Chem. Soc., 2012, vol. 134, pp. 9094-9097 (4 pages).
Mace, C.R. et al., "Manufacturing Prototypes for Paper-Based Diagnostic Devices," Microfluid. Nanofluidics, 2014, vol. 16, pp. 801-809 (9 pages).
Mara, D.D. et al., "Water- and Excreta-Related Diseases: Unitary Environmental Classification," J. Environ. Eng., 1999, vol. 125(4), pp. 334-339 (6 pages).
Martinez, A.W. et al., "Patterned Paper as a Platform for Inexpensive, Low-Volume, Portable Bioassays," Angew. Chem. Int. Ed. 2007, vol. 46, pp. 1318-1320 (3 pages).
Martinez, A.W. et al., "Three-Dimensional Microfluidic Devices Fabricated in Layered Paper and Tape," Proc. Natl. Acad. Sci. USA, Dec. 16, 2008, vol. 105, No. 50, pp. 19606-19611 (6 pages).
Martinez, A.W. et al., "Simple Telemedicine for Developing Regions: Camera Phones and Paper-Based Microfluidic Devices for Real-Time, Off-Site Diagnosis," Anal. Chem., 2008, vol. 80, pp. 3699-3707 (9 pages).
Mentele, M.M. et al., "Microfluidic Paper-Based Analytical Device for Particulate Metals," Anal. Chem. 2012, vol. 84, pp. 4474-4480 (7 pages).
Miltenyi, S. et al, "High Gradient Magnetic Cell Separation with MACS," Cytometry, 1990, vol. 11, pp. 231-238 (8 pages).
Mirica, K.A. et al., "Magnetic Levitation in the Analysis of Foods and Water," J. Agric. Food Chem., 2010, vol. 58, pp. 6565-6569 (5 pages).
Mirica, K.A. et al., "Mechanical Drawing of Gas Sensors on Paper," Angew. Chem. Int. Ed., Oct. 22, 2012, vol. 51(43), pp. 10740-10745 (11 pages).
Mosadegh, B. et al., "A Paper-Based Invasion Assay: Assessing Chemotaxis of Cancer Cells in Gradients of Oxygen," Biomaterials, 2015, vol. 52, pp. 262-271 (10 pages).
Mosmann, T., "Rapid Colorimetric Assay for Cellular Growth and Survival: Application to Proliferation and Cytotoxicity Assays," J. Immunol. Methods, 1983, vol. 65, pp. 55-63 (9 pages).

Müller, R.H. et al., "Automatic Paper Chromatography," Anal. Chem., Sep. 1949, vol. 21, No. 9, pp. 1123-1125 (3 pages).
Myers, G.J. et al., "Point of Care Hematocrit and Hemoglobin in Cardiac Surgery: A Review," Perfusion, 2007, vol. 22, 179-183 (5 pages).
Nakamura, T. et al., "Interaction of Saponins with Red Blood Cells as Well as with the Phosphatidylcholine Liposomal Membranes," J. Pharm. Dyn., 1979, vol. 2, pp. 374-382 (9 pages).
Neu, B. et al., "Effects of Dextran Molecular Weight on Red Blood Cell Aggregation," Biophys J., Sep. 2008, vol. 95, pp. 3059-3065 (7 pages).
Nie, Z. et al., "Electrochemical Sensing in Paper-Based Microfluidic Devices." Lab Chip, 2010, vol. 10, pp. 477-483 (7 pages).
Nie, Z. et al., "Integration of Paper-Based Microfluidic Devices with Commercial Electrochemical Readers," Lab Chip, 2010, vol. 10, pp. 3163-3169 (7 pages).
Noh, H. et al., "Fluidic Timers for Time-Dependent, Point-of-Care Assays on Paper," Anal. Chem., 2010, vol. 82, pp. 8071-8078 (8 pages).
Noiphung, J. et al., "A Novel Paper-Based Assay for the Simultaneous Determination of Rh Typing and Forward and Reverse ABO Blood Groups." Biosens. and Bioelectron. May 15, 2015, vol. 67, pp. 485-489 (5 pages).
Orskov, F. et al., "*Escherichia coli* Serotyping and Disease in Man and Animals," Can. J. Microbiol., 1992, vol. 38, pp. 699-704 (7 pages).
Papadopoulos, N.G. et al., "An Improved Fluorescence Assay for the Determination of Lymphocyte-Mediated Cytotoxicity Using Flow Cytometry," J. Immunol. Methods, 1994, vol. 177, pp. 101-111 (11 pages).
Park, T.S. et al., "Smartphone Quantifies *Salmonella* from Paper Microfluidics," Lab Chip, 2013, vol. 13, pp. 4832-4840 (9 pages).
Peeling, R.W. et al., "Rapid Tests for Sexually Transmitted Infections (STIs): The Way Forward," Sex. Transm. Infect., 2006, vol. 82 (Suppl V), pp. v1-v6 (6 pages).
Pollock, N.R. et al., "A Paper-Based Multiplexed Transaminase Test for Low-Cost Point-of-Care Liver Function Testing," Sci. Transl. Med., Sep. 19, 2012, vol. 4, Issue 152, pp. 1-10 (12 pages).
Pollock, N.R. et al., "Field Evaluation of a Prototype Paper-Based Point-of-Care Fingerstick Transaminase Test," PLoS One, Sep. 2013, vol. 8, Issue 9, e75616, pp. 1-10 (10 pages).
Posthuma-Trumpie, G.A. et al., "Lateral Flow (Immune)Assay: Its Strengths, Weaknesses, Opportunities and Threats. A Literature Survey," Anal. Bioanal. Chem., 2009, vol. 393, pp. 569-582 (14 pages).
Ramirez-Castillo, F.Y. et al., "Waterborne Pathogens: Detection Methods and Challenges," Pathogens, 2015, vol. 4, pp. 307-334 (28 pages).
Sampson, S. et al., "Platelet Rich Plasma. Injection Grafts for Musculoskeletal Injuries: A Review," Curr. Rev. Musculoskelet. Med., 2008, vol. 1, pp. 165-174 (10 pages).
Sapsford, K.E. et al., "Indirect Competitive Immunoassay for Detection of Alfatoxin $B_1$ in Corn and Nut Products Using the Array Biosensor," Biosens. Bioelectron., 2006, vol. 21, pp. 2298-2305 (8 pages).
Sato, S. et al., "Enhanced Expression of CD71, Transferrin Receptor, on Immature Reticulocytes in Patients with Paroxysmal Nocturnal Hemoglobinuria," Int. J. Lab. Hematol., 2010, vol. 32, pp. e137-e143 (7 pages).
Schonhorn, J.E. et al., "A Device Architecture for Three-Dimensional, Patterned Paper Immunoassays," Lab Chip, 2014, vol. 14, pp. 4653-4658 (6 pages).
Shapiro, N.D. et al., "Measuring Binding of Protein to Gel-Bound Ligands Using Magnetic Levitation," J. Am. Chem. Soc., 2012, vol. 134, pp. 5637-5646 (10 pages).
Shen, L. et al., "Point-of-Care Colorimetric Detection with a Smartphone," Lab Chip, 2012, vol. 12, pp. 4240-4243 (4 pages).
Smit, P.W. et al., "Systematic Review of the Use of Dried Blood Spots for Monitoring Hiv Viral Load and for Early Infant Diagnosis," PLoS One, Mar. 2014, vol. 9, Issue 3, e86461, pp. 1-8 (8 pages).

(56) References Cited

OTHER PUBLICATIONS

Smith, C.A. et al., "Antibodies to CD3/T-Cell Receptor Complex Induce Death by Apoptosis in Immature T Cells in Thymic Cultures," Nature, Jan. 12, 1989, vol. 337, pp. 181-184 (4 pages).
Songjaroen, T. et al., "Blood Separation on Microfluidic Paper-Based Analytical Devices," Lab Chip, 2012, vol. 12, pp. 3392-3398 (7 pages).
Soohoo, J.R. et al., "Microfluidic Aqueous Two Phase System for Leukocyte Concentration From Whole Blood," Biomed. Microdevices, 2009, vol. 11, pp. 323-329 (7 pages).
Su, S. et al., Adsorption and Covalent Coupling of ATP-Binding DNA Aptamers Onto Cellulose, Langmuir, 2007, vol. 23, pp. 1300-1302 (3 pages).
Thom, N.K. et al., "'Fluidic-Batteries' as Low-Cost Sources of Power in Paper-Based Microfluidic Devices," Lab Chip, 2012, vol. 12, pp. 1768-1770 (3 pages).
Tominaga, H. et al., "A Water-soluble Tetrazolium Salt Useful for Colorimetric Cell Viability," Anal. Commun., 1999, vol. 36, pp. 47-50 (4 pages).
Vella, S.J. et al., "Measuring Markers of Liver Function Using a Micropatternd Paper Device Designed for Blood for a Fingerstick," Anal. Chem., 2012, vol. 84, pp. 2883-2891 (9 pages).
Vivid Plasma Separation Membrane, available at https://shop.pall.com/INTERSHOP/web/WFS/PALL-PALLUS-Site/en_US/-USD/ViewProduct-Start?SKU=gri7811s&CatalogID=Medical&_ga=2.58868520.406528151.1537301592-1455097616.1537301592, accessed on Jul. 18, 2015 (6 pages).
Voller, A. et al., "Enzyme Immunoassays with Special Reference to ELISA Techniques," J. Clin. Pathol., 1978, vol. 31, pp. 507-520 (14 pages).
Walters, J.; Garrity, P. "Performance Evaluation of the Sysmex XE-2100 Hematology Analyzer," Lab Hematol., 2000, vol. 6, pp. 83-92 (10 pages).
Wardlaw, S.C. et al., "Quantitative Buffy Coat Analysis," J. Am. Med. Assoc., Feb. 4, 1983, vol. 249, No. 5, pp. 617-620 (4 pages).
Wong, A.P. et al., "Egg Beater as Centrifuge: Isolating Human Blood Plasma from Whole Blood in Resource-Poor Settings," Lap Chip, 2008, vol. 8, pp. 2032-2037 (6 pages).
Yang, X. et al., "A Simple, Rapid, Low-Cost Diagnostic Test for Sickle Cell Disease," Lab Chip, 2013, vol. 13, pp. 1464-1467 (5 pages).
Yetisen, A.K. et al., "Paper-based microfluidic point-of-care diagnostic devices," Lab Chip, 2013, vol. 13, pp. 2210-2251 (42 pages).
Yu, D. et al., "Paper-PEG-based Membranes for Hydrophobic Interaction Chromatography: Purification of Monoclonal Antibody," Biotechnol. and Bioeng., Apr. 14, 2008, vol. 99, No. 6, pp. 1434-1442 (9 pages).
Yu, D.T.Y. et al., "Human Lymphocyte Subpopulations. Effect of Corticosteroids," J. Clin. Invest., Feb. 1974, vol. 53, pp. 565-571 (7 pages).
Ziegler-Heitbrock, L. et al., "Nomenclature of Monocytes and Dendritic Cells in Blood," Blood, Oct. 21, 2010, vol. 116, No. 16, e74-e80 (8 pages).
Zola, H. et al., "CD Molecules 2005: Human Cell Differentiation Molecules," Blood, Nov. 1, 2005, vol. 106, No. 9, pp. 3123-3126 (5 pages).
International Search Report and Written Opinion in International Patent Application No. PCT/US2017/013065, dated May 18, 2017 (13 pages).

\* cited by examiner

10μL sample, 10 min runtime

| Cell Type | Source | Cell | Surface Markers |
|---|---|---|---|
| Neutrophil | Whole blood | Primary | CD16, CD66b |
| Basophil | ATCC, Celprogen, whole blood | KU812, primary | CD193, FcεRI |
| Eosinophil | ATCC, RIKEN, whole blood | HL60 clone 15, EoL-1, primary | siglec-8, CD32 |
| Monocyte | ATCC, whole blood | AML-193, primary | CD35, CD14 |
| B lymphocyte | ATCC, whole blood | MAVER-1, primary | CD19, CD21 |
| T lymphocyte | ATCC, whole blood | CEM-T4, H9, Jurkat, primary | CD3, CD4 |
| Total WBC | Cocktail of isolated cell types | | CD45 |

FIG. 19

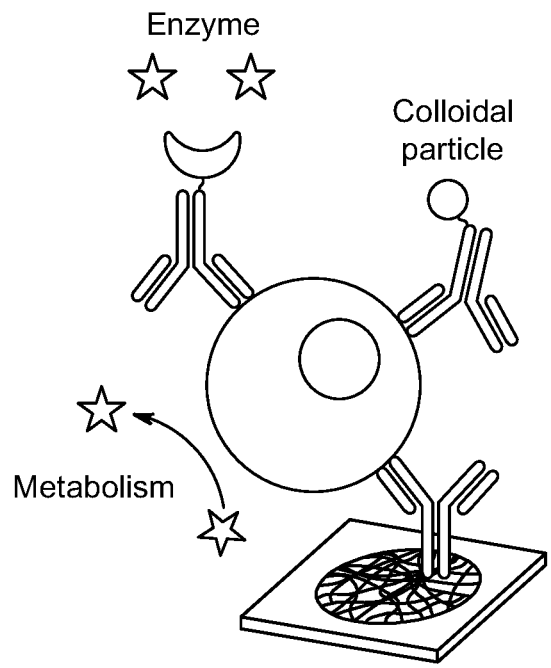
FIG. 20A
| Metabolism | Enzyme | Other |
|---|---|---|
| Resazurin | HRP | Colloid |
| WST-8 | Gox | Photoinitiator |
| | β-Gal | |
FIG. 20B
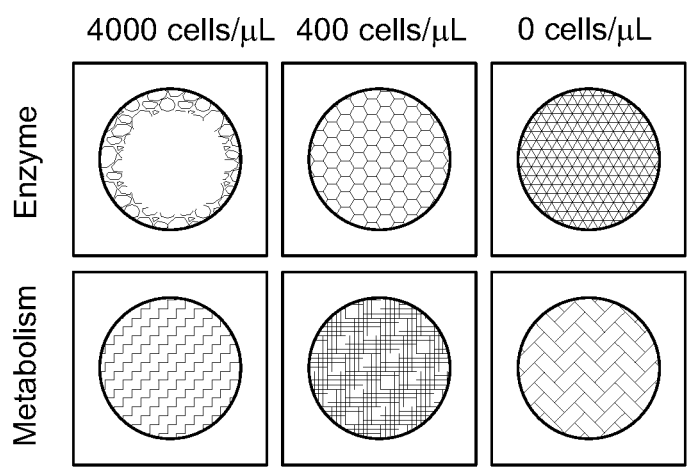
FIG. 20C

0 (Cells)

500

1000

2000

3000

4000

Cells: MDA-MB-231
coating: 5F7

Cells: SK-BR-3
coating: None

Cells: SK-BR-3
coating: 5F7

SEPARATION OF CELLS BASED ON SIZE AND AFFINITY USING PAPER MICROFLUIDIC DEVICE

CROSS-REFERENCE TO RELATED APPLICATIONS

This application is a national stage bypass continuation-in-part of International Application No. PCT/US2017/013065, filed on Jan. 11, 2017, and titled "Separation Of Cells Based On Size And Affinity Using Paper Microfluidic Device," which claims priority to and benefit of U.S. Provisional Patent Application Ser. No. 62/277,810, filed on Jan. 12, 2016, and titled "Separation Of Cells Based On Size And Affinity Using Paper Microfluidic Device," each of which is hereby incorporated by reference herein in its entirety.

FIELD OF THE INVENTION

The present invention relates generally to paper-based analytical and bioanalytical sensors for separation, detection, and quantification of cells from complex samples.

BACKGROUND OF THE INVENTION

Paper-based microfluidic devices have emerged as a platform that is capable of supporting the development of a number of useful analytical and bioanalytical sensors, the capabilities of which range from the detection of environmental contaminants to metabolites in blood plasma. Paper-based sensors often produce colorimetric results, which allow data to be interpreted rapidly at the point-of-use in a manner that is either qualitative (i.e., by eye) or quantitative through the use of simple readers. Utilizing paper as a substrate to develop analytical assays is beneficial because the infrastructure required to produce the analytical assays is minimal (e.g., a printer, heating element, and pipette), raw materials are inexpensive and ubiquitous (cents per sheet), and devices can be prototyped rapidly (within minutes from conception to use). By patterning paper with hydrophobic barriers, hydrophilic channels can be designed to control the wicking of fluids by capillary action. Complex, three-dimensional microfluidic networks can be fabricated from either stacking multiple layers of paper or folding a single layer of paper (i.e., origami). Simple design rules provide access to many different architectures of fluidic networks, which can facilitate the manufacture of devices that range from one-step, field-deployable diagnostic tools to sophisticated paper "machines."

With the considerable interest in this field of research, a glaring oversight has been the lack of applications of paper-based microfluidic devices for the separation or detection of cells. This omission appears to be caused based on a perspective in which paper is viewed as a passive substrate, instead of being viewed as a component that is fundamental to the function of the microfluidic device. Consequently, paper has been applied only to the filtration of all cells from plasma or to the separation of misformed (i.e., sickled) red blood cells, or as a scaffold for the study of cultures of mammalian cells. However, the ability to detect cells has significant value in applications related to, among others, personalized healthcare, monitoring of livestock, and determining the quality of food and water. These important capabilities are currently only available in established economies with centralized laboratories that are equipped with modern instrumentation and that include an educated workforce. Consequently, a significant percentage of the world's population—particularly those living in low-income and middle-income countries—have limited access to tools that could drastically improve the quality of life. Accordingly, paper has the potential to enable new classes of biological separations, analytical sensors, and point-of-use assays for underrepresented populations across the globe.

SUMMARY OF THE INVENTION

According to one aspect of the present disclosure, a three-dimensional ("3D") microfluidic device is capable of supporting the development of analytical and bioanalytical sensors. The device allows for separation and/or quantification of the cells in whole human blood via size-exclusion determined by pore size and via affinity separation by biochemical functionalization of a porous material, such as paper, as described below in reference to the drawings. By way of example, the potential of the microfluidic device is directed to at least a future new low-cost platform for the identification of a critical hematological index (hematocrit), i.e., the ratio of packed red blood cell volume to total blood volume. Additional potential applications include personalized healthcare, monitoring of livestock, and determining the quality of food and water.

According to one aspect of the present disclosure, a microfluidic device, includes a first layer of a porous material with pores having a first average pore size, the first layer having a liquid-receiving area through which a liquid sample is received into the microfluidic device. A second layer of another porous material, which is the same or different than the porous material of the first layer, is stacked below the first layer, the second layer having pores of a second average pore size. A channel is positioned within the second layer and has a starting end positioned at least in part in an overlapping manner with the liquid-receiving area. The channel has a terminating end extending laterally at a predetermined wicking distance from the starting end. The first average pore size and the second average pore size cause a wicking effect in which at least some of the liquid sample flows along the channel at least a portion of the wicking distance between the starting end and the terminating end.

According to another aspect of the present disclosure, a method is directed to providing a microfluidic device and includes providing a first layer of a porous material with pores having a first average pore size, the first layer having a liquid-receiving area through which a liquid sample is received into the microfluidic device. The method further includes stacking below the first layer a second layer of the same or different porous material having pores of a second average pore size, and positioning a channel within the second layer. The channel has a starting end positioned at least in part in an overlapping manner with the liquid-receiving area of the first layer, the channel having a terminating end extending laterally at a predetermined wicking distance from the starting end. The first average pore size and the second average pore size are selected such that, upon the receiving of the liquid sample, a wicking effect is caused in which at least some of the liquid sample flows along the channel at least a portion of the wicking distance between the starting end and the terminating end.

According to yet another aspect of the present disclosure, microfluidic device includes a sample-addition layer of a first porous material with pores having a first average pore size. The sample-addition layer has a liquid-receiving area through which a liquid sample is received into the microfluidic device. The microfluidic device further includes a sample-splitting layer located adjacent to the sample-addition layer, the sample-splitting layer having a first aperture for receiving a first portion of the liquid sample and a second aperture for receiving a second portion of the liquid sample. The microfluidic device also includes a separation membrane located adjacent to the first aperture of the sample-splitting layer, the separation membrane receiving only the portion of the liquid sample from the first aperture. The microfluidic device also includes a readout layer of a second porous material located adjacent the separation membrane, the second porous material having pores with a second average pore size that is different than the first average pore size. The readout layer has a first channel configured to receive in a starting end the first portion of the liquid sample from the sample-splitting layer, via the separation membrane. The first channel has a terminating end extending laterally at a predetermined wicking distance from the starting end, the first portion of the liquid sample flowing at least in part along the wicking distance to indicate a first value of the liquid sample. The readout layer further has a second channel positioned adjacent to the first channel for receiving the second portion of the liquid sample, the second channel including a stored reagent that reacts with the second portion of the liquid sample to indicate a second value of the liquid sample.

Additional aspects of the present invention will be apparent to those of ordinary skill in the art in view of the detailed description of various embodiments, which is made with reference to the drawings, a brief description of which is provided below.

BRIEF DESCRIPTION OF THE DRAWINGS

FIG. 19 is a table showing types of cells, their sources, and examples of surface markers to develop paper-based cytometers based on positive selection.

FIG. 20A illustrates a schematic of assay in which captured by surface marker-specific antibodies immobilized on paper and detected using a variety of colorimetric indicators.

FIG. 20B is a table detailing several methods for detecting captured cells based on metabolism or antibody conjugated to a detector.

FIG. 20C illustrates preliminary data showing detection of CD4+T lymphocytes in paper cytometers at clinically high and low cell counts using either anti-CD4-HRP (with TMB substrate) or WST-8 as reporters.

Figure 1A:
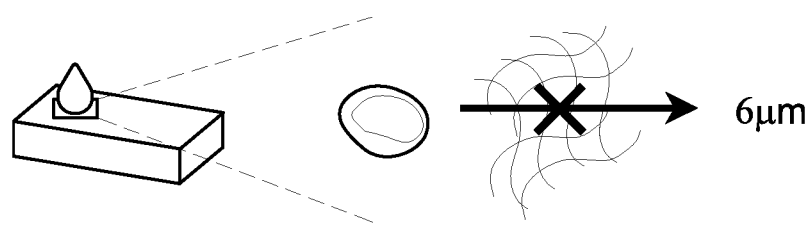
FIG. 1A is an illustration showing selection of paper pore sizes for preventing migration of cells.

While the invention is susceptible to various modifications and alternative forms, specific embodiments have been shown by way of example in the drawings and will be described in detail herein. It should be understood, however, that the inventions are not intended to be limited to the particular forms disclosed. Rather, the aspects disclosed herein cover all modifications, equivalents, and alternatives falling within the spirit and scope of the invention as defined by the appended claims.

DETAILED DESCRIPTION

While aspects of the present disclosure are susceptible of embodiment in many different forms, there is shown in the drawings and will herein be described in detail some embodiments with the understanding that the present disclosure is to be considered as an exemplification of the principles of the embodiments and is not intended to limit the broad aspect of the inventions to the embodiments illustrated. For purposes of the present detailed description, the singular includes the plural and vice versa (unless specifically disclaimed); the words "and" and "or" shall be both conjunctive and disjunctive; the word "all" means "any and all"; the word "any" means "any and all"; and the word "including" means "including without limitation."

Paper-based microfluidic devices are useful in the separation and quantification of cells in human blood based on two principles: (i) size-exclusion, in which a paper is selected with an ideal pore size to permit or restrict the flow of cells through a device; and (ii) affinity separation, in which a paper is biochemically functionalized to capture a specific cell of interest based on its expression of surface markers. The microfluidic devices described below in reference to the drawings are based on these two principles and bring cell-counting capabilities directly into hands of users at a point-of-need, with the potential to revolutionize diagnostics in a manner similar to, for example, the introduction of the home pregnancy test.

The microfluidic devices include paper-based analytical and bioanalytical sensors with features that focus at least in part on separation, detection, and quantification of cells from complex samples. The manufacturing of the microfluidic devices provides simple, yet functional, devices from layers of paper and tape, for example. In other examples, instead of or in addition to paper, microfluidic device include any porous materials configured or selected with the proper pore size. The microfluidic devices (i) are designed to allow the incorporation of a number of fluidic operations into paper-based analytical sensors, and (ii) are capable of controlling (i.e., permitting or impeding) the wicking of cells based on the pore sizes of the papers and through modifications of the chemical properties of the paper fibers through simple chemical functionalization reactions. A further benefit of the microfluidic devices is the ability to manufacture paper-based analytical sensors reproducibly and in large volumes, e.g., hundreds of millions of devices per year per test. Additional benefits of the microfluidic devices include (i) environmental monitoring of toxic or contaminating species, (ii) separations of complex mixtures of biological and non-biological matter, (iii) the study of interactions between microbes and hosts, and (iv) the development of diagnostic assays that are designed specifically for use in the developing world and limited-resource settings.

Figure 1B:
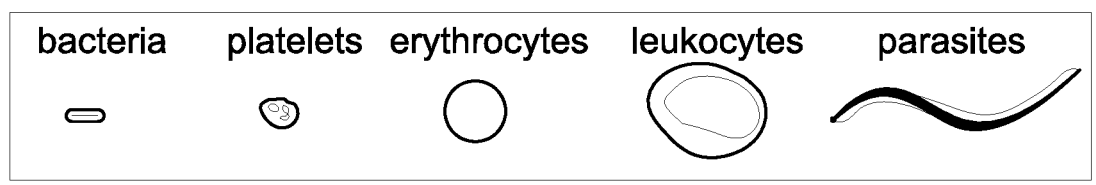
FIG. 1B is an illustration showing a broad range of cell sizes.
Figure 1C:
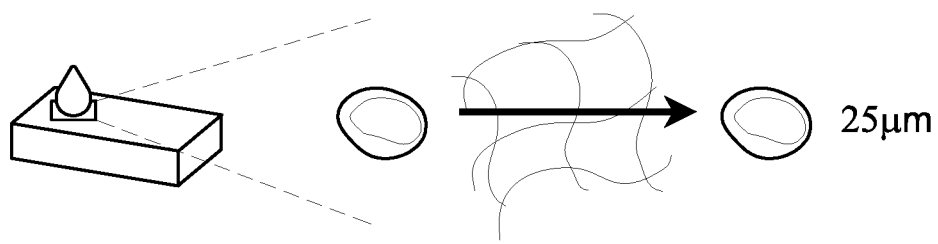
FIG. 1C is an illustration showing selection of paper pore sizes for permitting migration of cells.

Referring to FIGS. 1A-1C, the use of cells in paper for bioanalytical assays has thus far been limited to those applications where cells are either impregnated into paper (e.g., to study the effects of nutrient gradients on the growth of cells and models for tumor formation) or filtered by the paper (e.g., for the detection of sickled red blood cells or to perform blood-typing assays). In both examples, paper serves as a medium for the broad exclusion or filtration of cells. One factor that has limited the development of paper-based assays for the detection of cells is the choice of material. As illustrated in FIG. 1A, a substrates selected—typically, Whatman chromatography paper Grade no. 1—do not wick mammalian cells due to their small average pore size. The use of materials with small pore sizes in paper-based devices is historical, rather than an absolute requirement. Hundreds of different grades of paper are available commercially and provide different combinations of pore sizes (ca. 0.2-200 µm), pore size distributions, thicknesses, surface areas, and overall chemical composition (e.g., cellulose-based or polymer-based). Cells also span a similarly large range of sizes, as illustrated in FIG. 1B. It follows, as illustrated in FIG. 1C, that a grade of paper could be selected that permits the migration of cells through a paper microfluidic device based on size. The broad range of available pore sizes facilitates the use of stacks of paper as size-exclusion media that selectively separates and isolates cells.

Figure 2A:
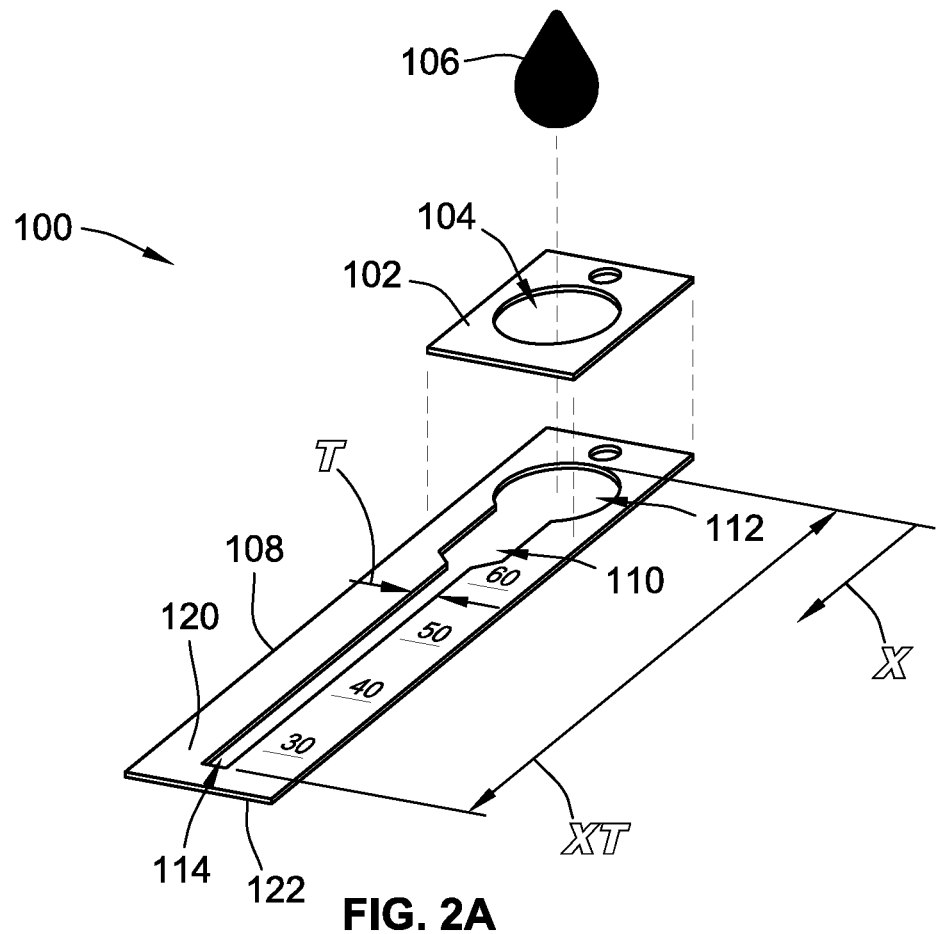
FIG. 2A is an illustration of a disassembled 2-layer microfluidic device.
Figure 2B:
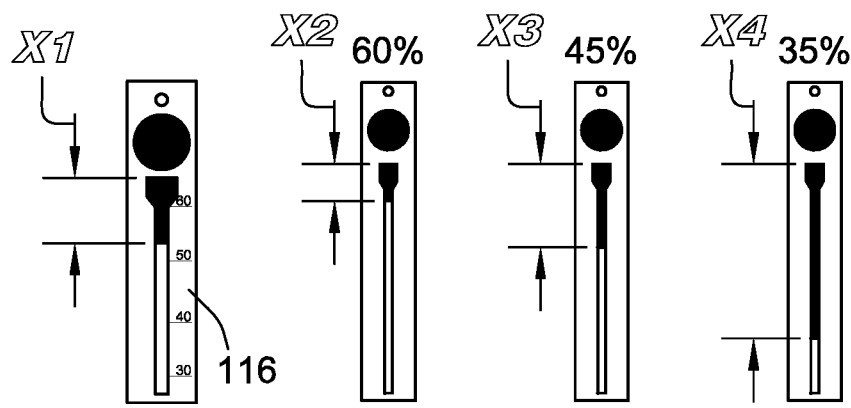
FIG. 2B is an illustration of the microfluidic device of FIG. 2A shown in assembled form and indicating different hematocrits.

Referring to FIGS. 2A and 2B, a number of papers are characterized for their ability to permit or restrict the wicking of erythrocytes (i.e., red blood cells). Focusing on erythrocytes as a model system offers three important benefits: (i) they are available as stabilized and relatively purified suspensions in buffer; (ii) they are available in whole blood; and (iii) the ability to quantify their concentration provides a critical hematological index, the hematocrit. The hematocrit is the volume fraction of packed erythrocytes in whole blood—the ratio of packed red blood cell (RBC) volume to the total blood volume. Aberrant hematocrit values are related to diseases that are common in the developing world (e.g., anemia and dehydration). By way of example, in a healthy adult, the hematocrit is typically in the range of about 36%-48% for women and 42%-52% for men. Deviations from these ranges are typically indicative of diseases, such as anemia, which is indicated in lower percentages in patients, and dehydration, which is indicated at higher percentages in patients. Currently, measurements of the hematocrit require either a hematology analyzer or a centrifuge. Neither instrument is readily available in limited-resource settings, but their analytical capabilities are greatly needed.

For example, as illustrated in FIG. 2A, the properties of paper are used to measure the hematocrit using a distance X erythrocytes wicked laterally within a paper-based microfluidic device 100. The microfluidic device 100 includes a first (top) layer of paper 102 with a liquid-receiving area 104 through which a liquid sample 106 is received into the microfluidic device 100. The first layer of paper 102 has a first average pore size that functions as a filter and, for example, restricts flow of white cells.

The microfluidic device 100 further includes a second (bottom) layer of paper 108 that is stacked below the first layer of paper 102. The second layer of paper 108 has pores of a second average pore size and includes a channel 110 with a thickness T. The channel 110 has a starting end 112 positioned at least in part in an overlapping manner with the liquid-receiving area 104 of the first layer of paper 102. The channel 110 has a terminating end 114 that extends laterally at a predetermined wicking distance XT from the starting end 112. The dimensions of the channel 110, including the wicking distance XT and the channel thickness, are selected based on one or more paper characteristics, such as average paper pore size, paper pore size distribution, the paper porosity, paper bubble point, and/or paper flow rate. According to one example, each layer 102, 108 is a cellulose-based paper, such as Ahlstrom chromatography paper. Optionally, the second layer of paper 108 is pretreated with ethylenediaminetetraacetic acid (EDTA) and/or sodium chloride (NaCl) to promote lateral flow of RBCs through the paper matrix formed by the microfluidic device 100.

As illustrated in FIG. 2B, the first average pore size of the first layer of paper 102 and the second average pore size of the second layer of paper 108 cause a wicking effect in which at least some of the liquid sample 106 flows along the channel 110 at least a portion of the wicking distance X between the starting end 112 and the terminating end 114. For example, the liquid sample 106 travels a first wicking distance X1 if the hematocrit percentage is approximately 55%, a second wicking distance X2 if the hematocrit percentage is approximately 60%, a third wicking distance X3 if the hematocrit percentage is approximately 45%, and a fourth wicking distance X4 if the hematocrit percentage is approximately 35%. Accordingly, the average pore size of the layers of paper 102, 108 is selected such that the liquid sample 106 fills the channel 110 a shorter wicking distance X if (a) the liquid sample 106 has a higher concentration of the cells of interest (e.g., RBCs) than if (b) the liquid sample 106 has a lower concentration of the cells of interest.

The channel 110 has a thicker initial area, which extends approximately the same distance as the second wicking distance X2, and a narrower secondary area that extends to the end of the total wicking distance XT. The thicker initial area is much thicker than the general thickness T of the channel 110 in the secondary area (as illustrated in FIG. 2A). The thicker initial area permits the wicking of higher hematocrits (e.g., >60%) laterally by having a wider (or thicker) initial channel area. The initial wide area provides sufficient area for a high concentration of cells to migrate through the channel 110 with minimal aggregation, while not wicking beyond the initial wide area. However, the thinner secondary area of thickness T is provided to obtain resolved wicking distances for lower hematocrits (e.g., 30%-55%). According to one example, the initial wide area is approximately 5 millimeters thick by 10 millimeters long, and the thinner secondary area of thickness T is approximately 2 millimeters thick by 40 millimeters long.

The hematocrit percentage is optionally indicated via one or more flow indicators 116 that indicate certain percentage marks (e.g., 60, 50, 40, and 30), in a thermometer-styled readout. According to the embodiment of FIGS. 2A and 2B, the flow indicators 116 are positioned on the second layer of paper 108. However, in other embodiments, the flow indicators 116 are positioned on the first layer of paper 102, or are positioned on both layers of paper 102, 108. Additionally, in other embodiments the flow indicators 116 are configured to indicate any cell concentration of a liquid sample (not just hematocrit percentages).

The layers of paper 102, 108 are stacked in direct contact with each other or are stacked in close proximity with each other. For example, the second layer of paper 108 is optionally separated from the first layer of paper 102 by an air gap to facilitate ease of wicking flow of the liquid sample 106. In another example, an intermediate layer is interposed between the layers of paper 102, 108 to facilitate the attachment of the layers of paper 102, 108 to each other. For example, the intermediate layer is a removable adhesive that facilitates the temporary affixing of the layers 102, 108 for ease of assembly and/or disassembly of the microfluidic device 100.

This exemplary approach relies on the obstruction of pores within the plane of the paper, which occurs in proportion to the concentration of erythrocytes that is applied to the device. That is, the pores within a layer of paper are easier to obstruct with relatively large numbers of erythrocytes than with a lower concentration of cells. As a result of a bottlenecking effect, high hematocrits stop migrating sooner than low hematocrits, and the inherent red color of the erythrocytes provides a label-free indication of signal transduction. The wicking distances X measured in paper-based devices correlate to hematocrits, which are optionally measured using standard techniques, and the wicking distance X that RBCs wick laterally is proportional to the hematocrit as measured in the flow channel 110. According to one test, the sample test duration (or incubation period) is approximately 30 minutes.

In accordance with the illustrated embodiment, the first layer of paper 102 extends only near the liquid-receiving area 104. However, in other embodiments, the first layer of paper 102 extends away from the liquid-receiving area 104. For example, in one alternative embodiment, the first layer of paper 102 is similar or identical in length to the second layer of paper 108.

In accordance with another alternative embodiment, the microfluidic device 100 includes a laminate layer 120 affixed to a top surface of the channel 110 to prevent or minimize flow of liquid away from the area near the channel 110, such as flow towards the first layer of paper 102. Additionally or alternatively, a laminate layer 122 is affixed to a bottom surface of the second layer of paper 108.

Figure 3A:
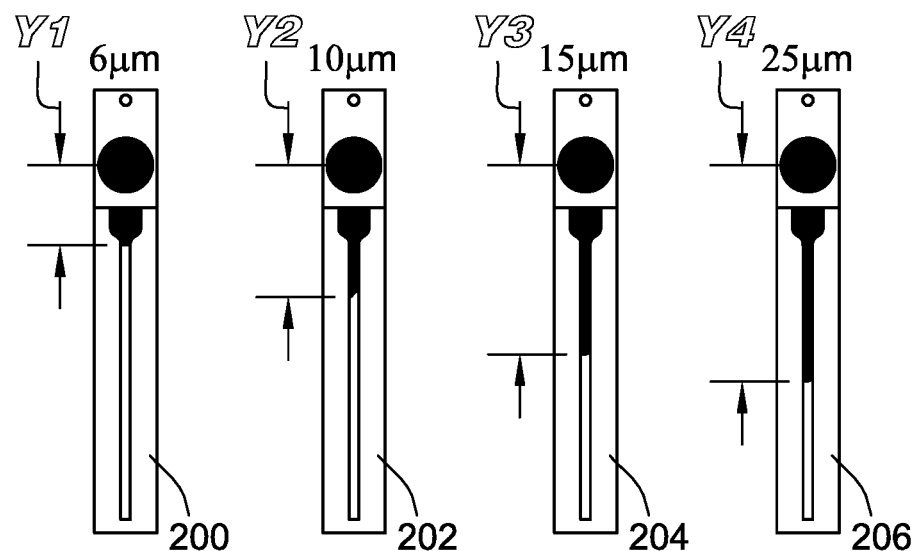
FIG. 3A is an illustration showing the effect of paper pore size on the performance of a plurality of paper-based hematocrit assays.

Referring to FIG. 3A, the effect of paper pore size on the performance of a paper-based hematocrit assay illustrates that small pore sizes restrict the transport of RBCs within a device, while larger pore sizes allow the RBC to migrate freely. Specifically, and by way of example only, a first microfluidic device 200 with a first average pore size of about 6 micrometers ($\mu$m) restrict the flow of RBCs to a first wicking distance Y1, a second microfluidic device 202 with a second average pore size of about 10 micrometers ($\mu$m) restrict the flow of RBCs to a second wicking distance Y2, a third microfluidic device 204 with a third average pore size of about 15 micrometers ($\mu$m) restrict the flow of RBCs to a third wicking distance Y3, and a fourth microfluidic device 206 with a fourth average pore size of about 25 micrometers ($\mu$m) restrict the flow of RBCs to a fourth wicking distance Y4. As the average pore size increases, so does the respective wicking distance.

Figure 3B:
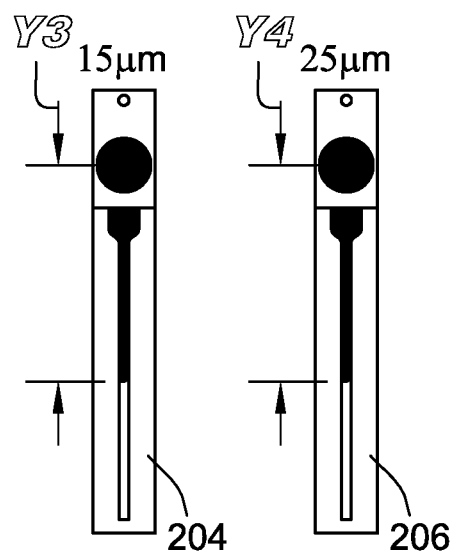
FIG. 3B is an illustration showing the effect of a threshold pore size on the performance of a paper-based hematocrit assay.

Referring to FIG. 3B, in an alternative embodiment and by way of a further example, the third average pore size of about 15 micrometers ($\mu$m) is a threshold pore size that designates a maximum limit beyond which the performance level remains approximately the same for the same hematocrit assay. Accordingly, in this alternative embodiment the performance remains the same for both the third average pore size of about 15 micrometers ($\mu$m) and for the fourth average pore size of about 25 micrometers ($\mu$m). In other words, the third and fourth wicking distances Y3 and Y4 are approximately the same.

Figure 4B:
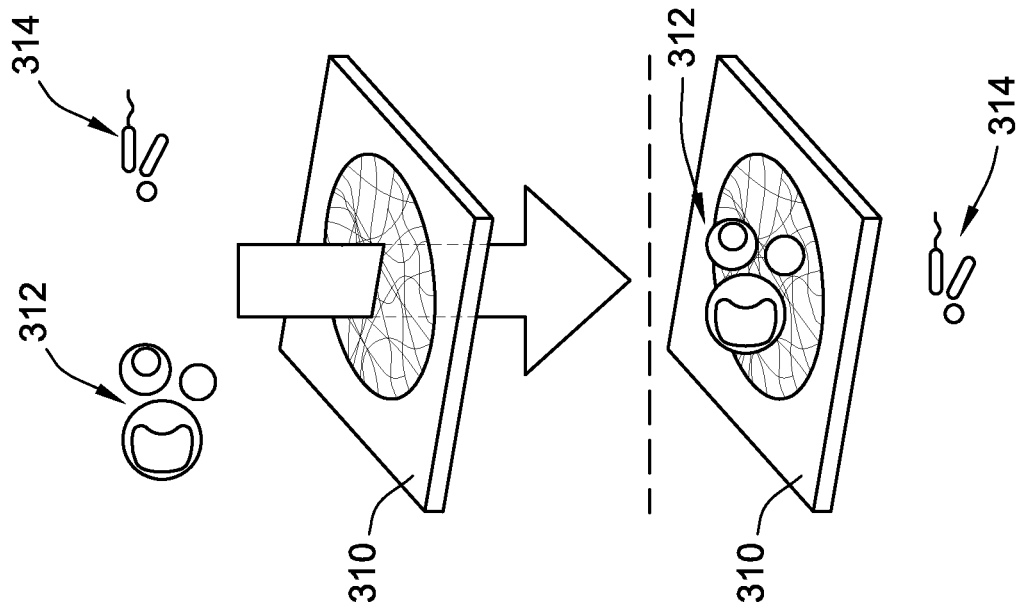
FIG. 4B is an illustration showing separation of somatic cells from bacteria.
Figure 4A:
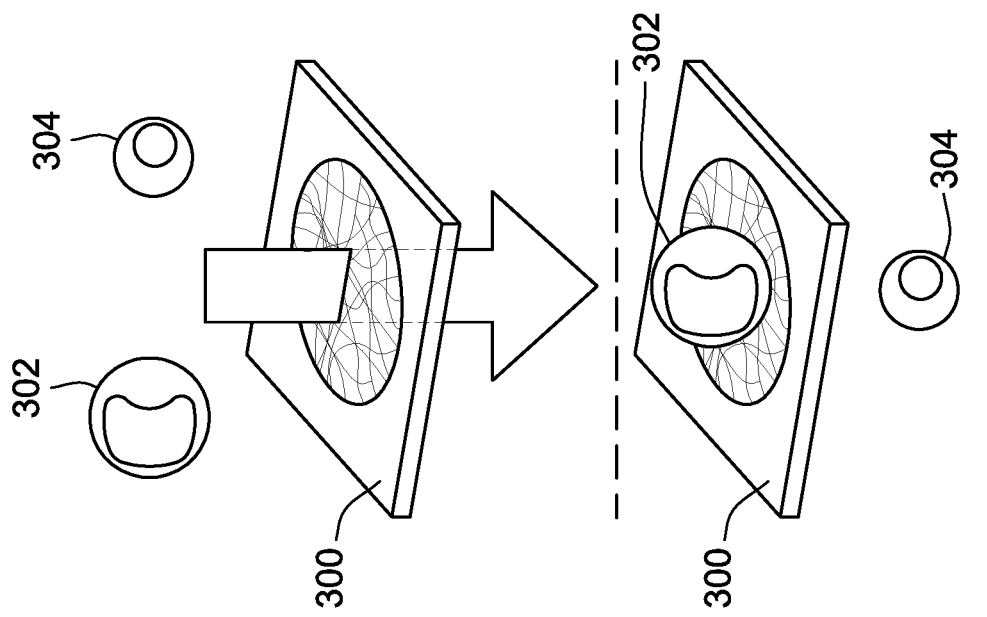
FIG. 4A is an illustration showing separation of large granulocytes from small lymphocytes.

Referring to FIG. 4A, separations of cells from complex media suggest the ability to fractionate populations of leukocytes contained in the buffy coat of blood into its different components (e.g., neutrophils and lymphocytes). The capability to, for example, separate neutrophils and lymphocytes provides an important hematological index related to leukocyte counts that is useful in assessing susceptibility to infections or undesirable side-effects caused by drug treatments. Thus, based on a size-exclusion feature in which differences in cell size is a determinative factor, a microfluidic device 300 has paper layers with pore sizes selected to separate large granulocytes 302 from small lymphocytes 304. The microfluidic device 300 prevents the large granulocytes 302 from passing through the microfluidic device 300, while the small lymphocytes 304 are permitted to pass through the microfluidic device 300.

Referring to FIG. 4B, the use of microfluidic paper-based devices is also expected to address the important topic of livestock health, which is related to food quality, by performing analytical assessments of the quality of milk from cows and goats. In such separations—related to spoilage or mastitis—the background components of milk (i.e., colloids of casein and milk fat globules) are highly heterogeneous and present a unique matrix from which contaminating cells (i.e., somatic cells and bacteria) are separated. For example, a microfluidic device 310 has paper layers with pore sizes to separate somatic cells 312 from bacteria 314.

Figure 5:
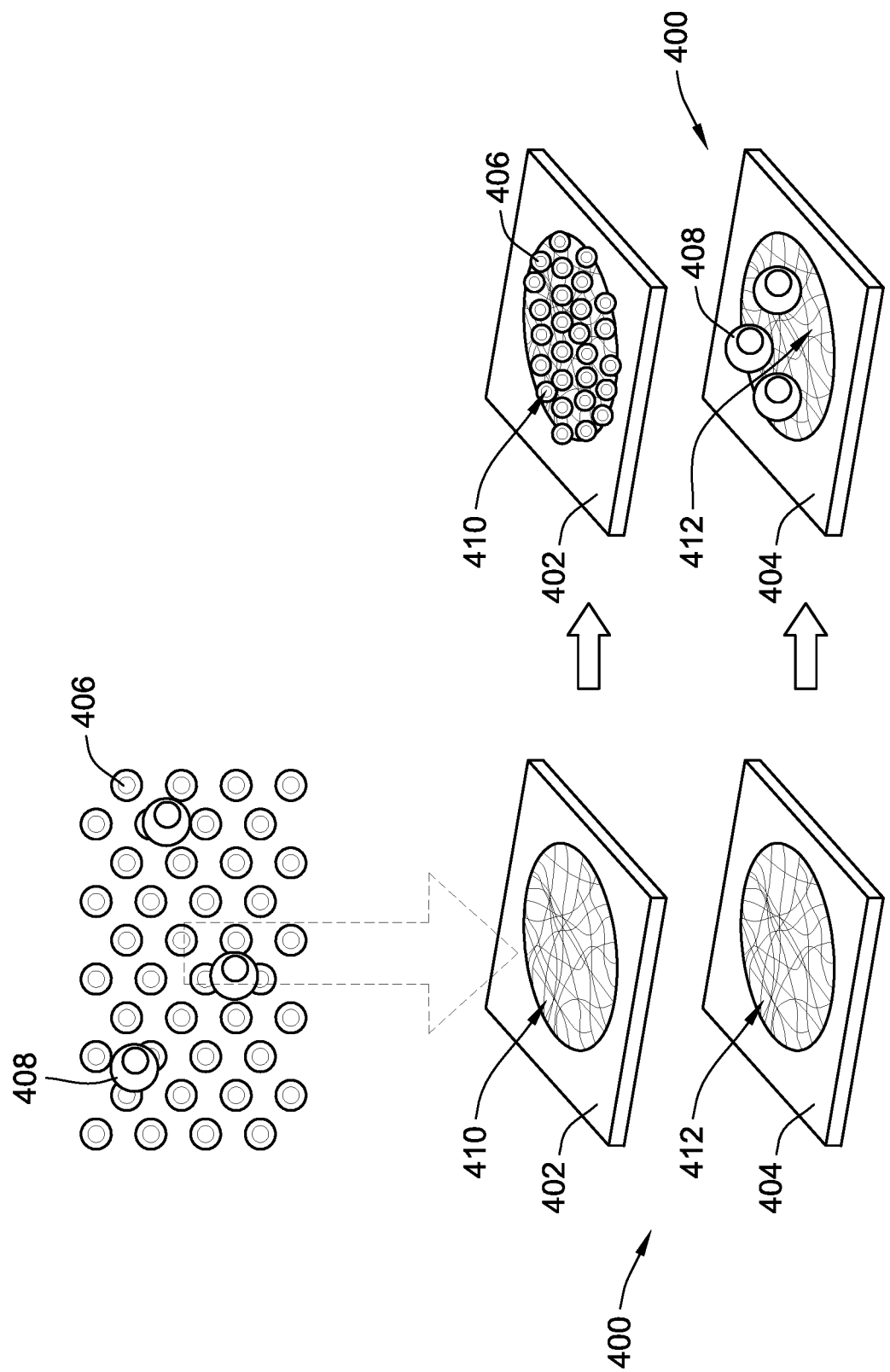
FIG. 5 is an illustrating showing separation of cells in paper based on partitioning, with erythrocytes (but not leukocytes) binding to paper that has been grafted with dextran.

Referring to FIG. 5, a microfluidic device 400 include a first layer of paper 402, with a polymer material 403 grafted onto the paper, and a second layer of paper 404. Erythrocytes 406—the major component of whole blood—are expected to present a significant source of interference for separations in which whole blood is the sample. If fractionation based on size is insufficient, additional and/or alternatives approaches are used to improve the quality of the separations. For example, in reference to differences in adhesive properties that exist between surfaces of erythrocytes 406 and leukocytes 408, an inexpensive polymer of glucose 403 (e.g., dextran) is to cause the aggregation of erythrocytes. Erythrocytes 406—and not leukocytes 408—partition preferentially into dextran-rich aqueous phases. Accordingly, based on this feature, the dextran material 403 that is grafted onto the first layer of paper 402 as a vehicle via which contaminating erythrocytes 406 are specifically removed from paper-based separation media.

The polymer material 403 can be any adhesive material that causes cells of a first type (e.g., erythrocytes 406) from a liquid sample to bind to the first layer of paper 402. Additionally, the average pore size of the first layer of paper 402 causes cells of a second type (e.g., leukocytes 408) to flow through a first liquid-receiving area 410 of the microfluidic device to a second liquid-receiving area 412. The second liquid-receiving area 412 is positioned at least in part in an overlapping manner with the first liquid-receiving area 410. The average pore size of the second layer of paper 404 causes the cells of the second type to wick through the second layer of paper 404.

In another exemplary approach, simple centrifugation methods (e.g., an egg-beater centrifuge) are used to stratify cells by density prior to introducing the fraction containing the least dense cells—rich in leukocytes—into paper-based devices. In yet another exemplary approach, a reagent (e.g., saponin) causes the selective hemolysis of erythrocytes. This approach likely requires devices to undergo rigorous washing to remove contaminants (e.g., hemoglobin) that are released by lysis.

Figure 6A:
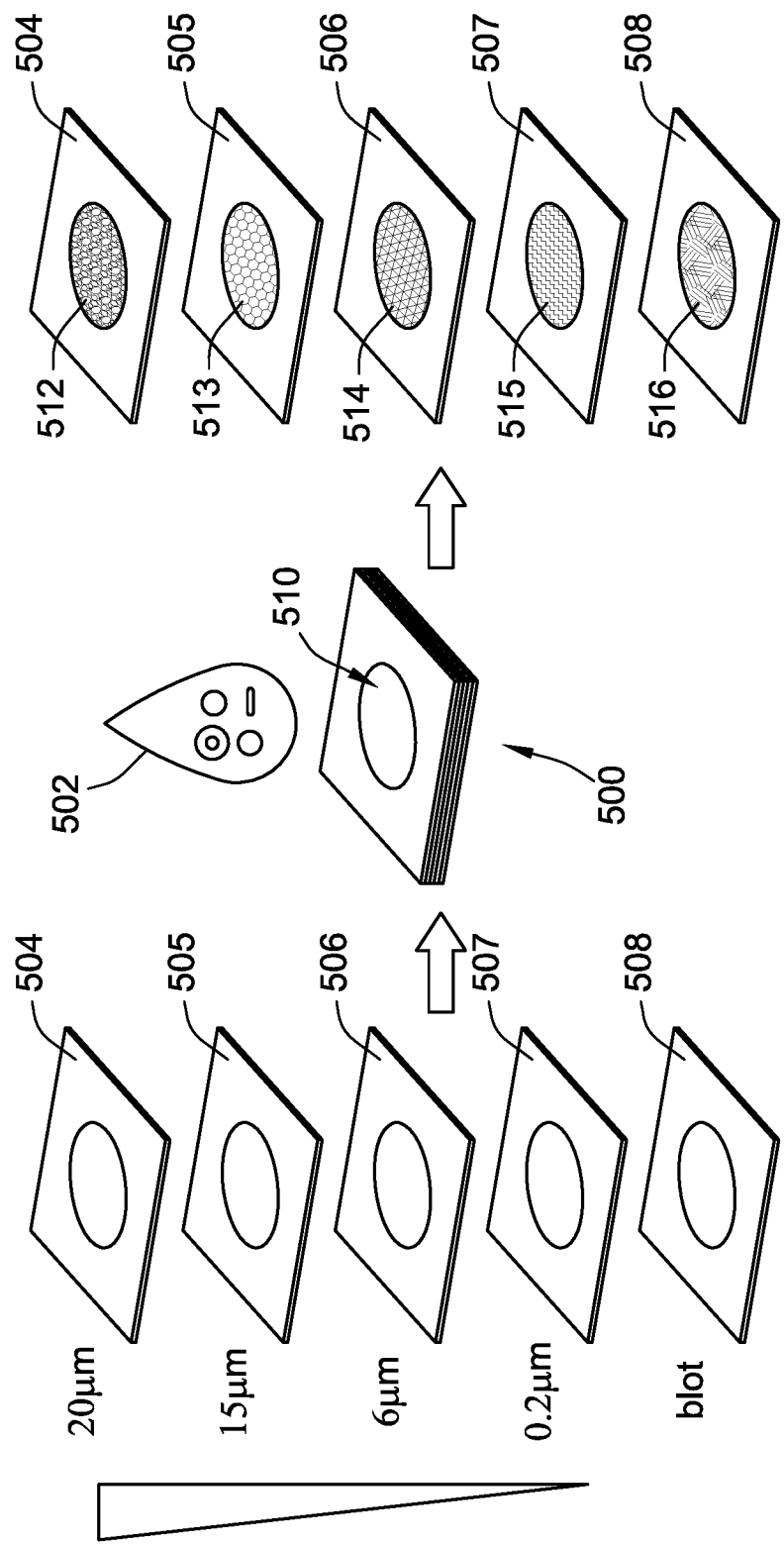
FIG. 6A is an illustration showing an integrated paper-based microfluidic device for separating multiple biological species from a single sample.

Referring to FIG. 6A, a comprehensive fractionation of cells from whole blood is achieved with a 3D microfluidic device 500 having multiple layers of stacked paper. The 3D microfluidic device 500 separates multiple biological species from a single liquid sample 502 based on the several layers of paper 504-508, with each layer being a different grade of paper with different pore sizes. Specifically, a first layer of paper 504 has an average pore size of about 20 micrometers ($\mu$all), a second layer of paper 505 has an average pore size of about 15 micrometers ($\mu$m), a third layer of paper 506 has an average pore size of about 6 micrometers ($\mu$m), a fourth layer of paper 507 has an average pore size of about 0.2 micrometers ($\mu$m), and a fifth layer of paper 508 includes a blot that does not include any cells, except potentially very small bacteria.

The microfluidic device 500 is assembled and the liquid sample 502 is added to a liquid-receiving area 510. The layers of paper 504-508 are stacked in an overlapping manner with respect to each other. Then, the microfluidic device 500 is disassembled and the layers of paper 504-508 are isolated to examine the separated cells. After disassembly, and by way of example, the first layer of paper 504 has retained only large white blood cells 512, the second layer of paper 505 has retained only small white blood cells 513, the third layer of paper 506 has retained only red blood cells 514, the fourth layer of paper 507 has retained only bacteria 515, and the fifth layer of paper 508 has retained plasma 516. In other words, each layer of paper 504-508 has an average pore size that is smaller than an average diameter of the respective cells of interest form the liquid sample 502. For example, the first layer of paper 504 has an average pore size—of about 20 micrometers (μm)—that is smaller than an average diameter of the large white blood cells 512.

Specific cell types and purified plasma is separated and stored within the layers of the 3D microfluidic device, which enables downstream and/or off-site analysis of samples of blood. In addition to using these separations in limited-resource settings, similar paper-based 3D microfluidic devices also enable: (i) purification of viruses from cell culture supernatants, and (ii) subsequent culture of microorganisms that have been separated using paper-based devices.

According to the illustrated embodiment, the average pore size decreases from the top layer 504 to the bottom layer 508. Based on specific applications, in accordance with other embodiments, the average pore size is the same in at least two of the plurality of layers 504-508 and/or the average pore size increases from the top layer 504 to the bottom layer 508.

Figure 6B:
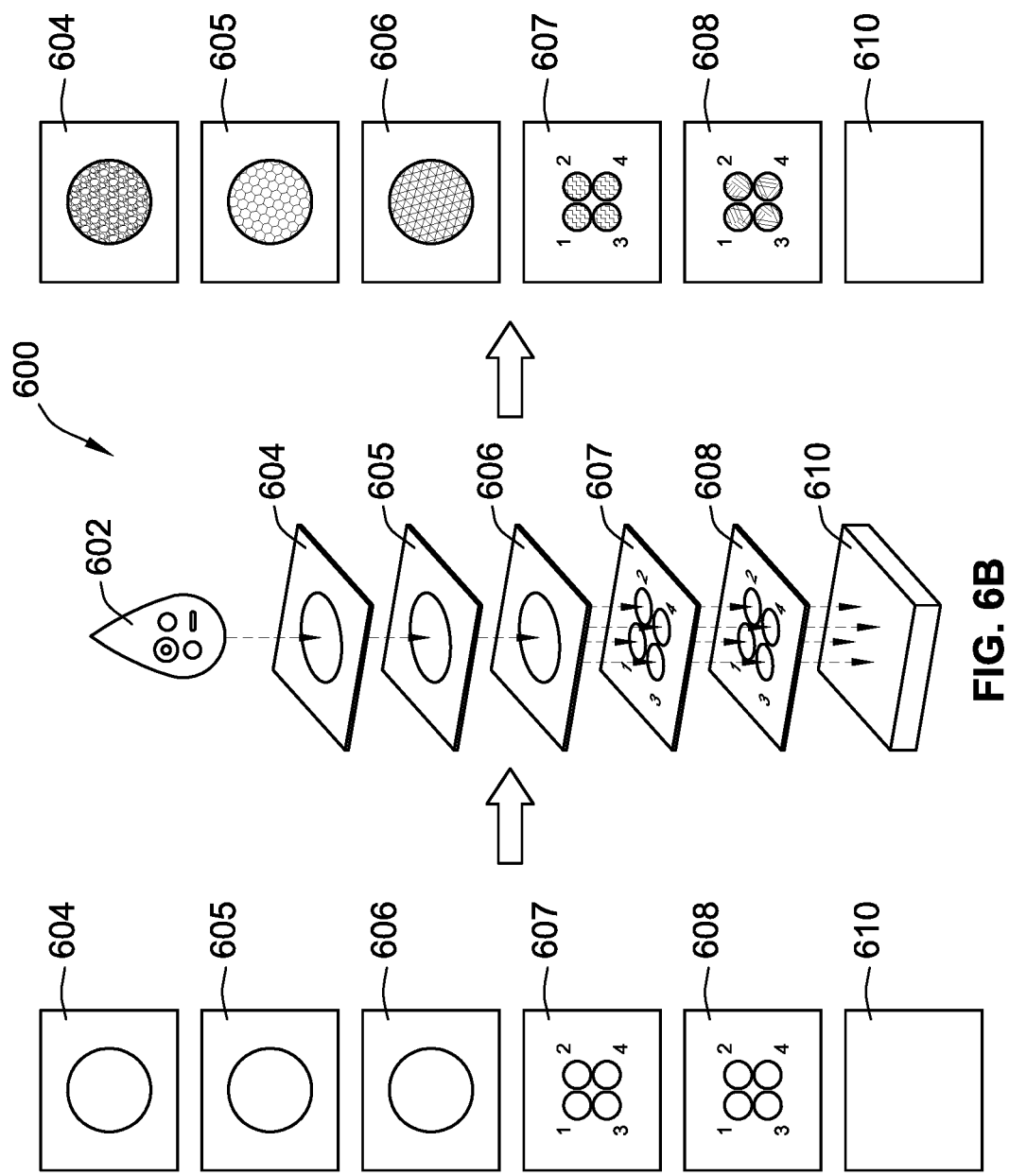
FIG. 6B is an illustration showing another integrated paper-based microfluidic device having multiple adhesive areas per layer for separating multiple biological species.

Referring to FIG. 6B, a 3D microfluidic device 600 has multiple layers of stacked papers for separating multiple biological species from a single liquid sample 602, based on several layers of paper 604-608. A blot 610 collects any remaining cells and/or fragments from the sample 602. The microfluidic device 600 is generally similar to the microfluidic device 500 illustrated in FIG. 6A, except that one or more of the paper layers 604-608 include a plurality of adhesive areas treated with the same or different adhesive materials.

By way of example, one or more of the paper layers 604-608 is treated with a cocktail of antibodies to separate and detect cells from the sample 602. For example, a second paper layer 605 is treated with a cocktail of antibodies including anti-CD71 and anti-CD47, and a third paper layer 606 is treated with a single type of antibodies—anti-CD34. The second and third paper layers 605, 606 are treated in a single area (similar to the layers of the microfluidic device 500). In contrast, each of a fourth layer 607 and a fifth layer 608 is treated with antibodies in multiple areas 1-4. For example, the fourth layer 607 is treated with anti-CD15 in area 1, anti-CD177 in area 2, anti-CD193 in area 3, and anti-siglec8 in area 4. The fifth layer 608 is treated with anti-CD3 in area 1, anti-CD14 in area 2, anti-CD16 in area 3, and anti-CD19 in area 4.

According to one example, in response to adding the sample 602 to the assembled layers of the microfluidic device 600, cells are separated and detected as follows. Reticulocytes and erythrocytes are separated and detected in the second layer 605, rare stem cells are recovered in the third layer 606, granulocytes are recovered in area 1 of the fourth layer 607, neutrophils are recovered in area 2 of the fourth layer 607, basophils are recovered in area 3 of the fourth layer 607, eosinophils are recovered in area 4 of the fourth layer 607, T lymphocytes are recovered in area 1 of the fifth layer 608, monocytes are recovered in area 2 of the fifth layer 608, NK cells are recovered in area 3 of the fifth layer 608, B lymphocytes are recovered in area 4 of the fifth layer 608, and other cells and/or fragments are recovered in the blot 610.

Figure 7:
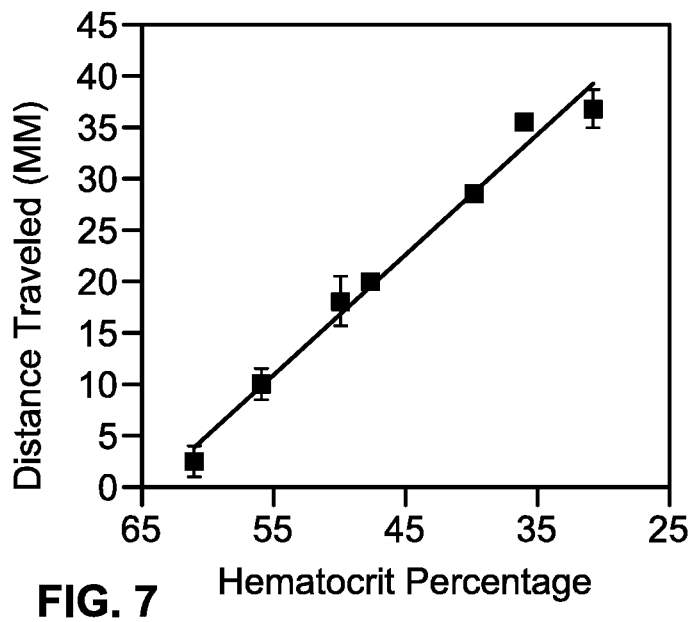
FIG. 7 is a graphical representation of various hematocrit percentages for samples of whole blood using microfluidic devices treated with sodium chloride and ethylenediaminetetraacetic acid (EDTA).

Referring to FIG. 7, the graphical representation shows various hematocrit percentages for samples of whole blood using microfluidic devices treated with sodium chloride and ethylenediaminetetraacetic acid (EDTA). The solid line is a linear fit of the data series ($R^2$=0.985). Each data point is the average of five replicates and the error bars are standard error of the mean.

Figure 8:
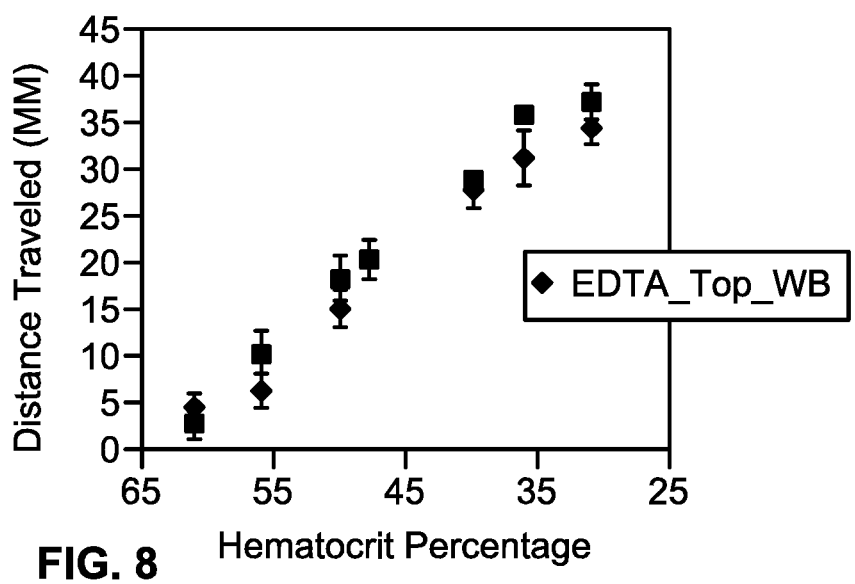
FIG. 8 is a graphical representation of various hematocrit percentages for samples of whole blood using microfluidic devices treated with EDTA on two different sections of the microfluidic devices.

Referring to FIG. 8, the graphical representation shows various hematocrit percentages for samples of whole blood using microfluidic devices treated with EDTA on two different sections of the microfluidic devices (i.e., top layer or bottom layer). The solid line is the linear fit of the data series. Each data point is the average of three replicates and the error bars are standard error of the mean.

Figure 9:
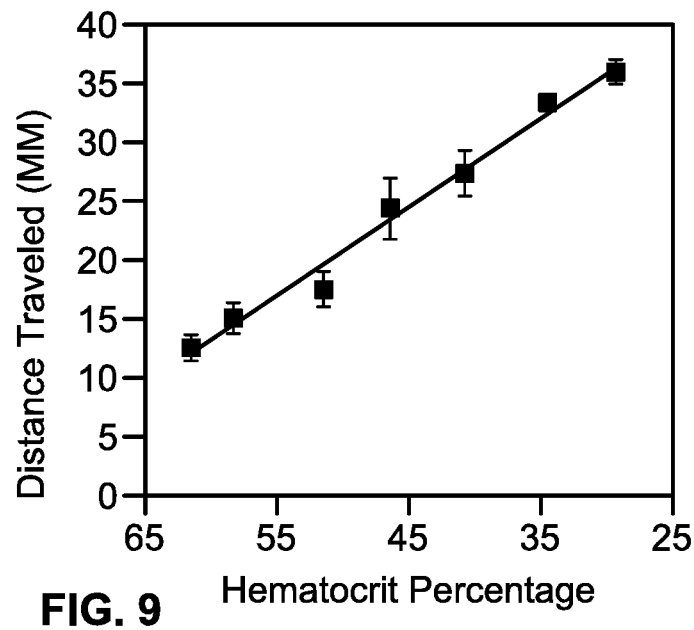
FIG. 9 is a graphical representation of various hematocrit percentages for samples of isolated red blood cells in Alsever's solution.

Referring to FIG. 9, the graphical representation shows various hematocrit percentages for samples of isolated red blood cells in Alsever's solution. The solid line is a linear fit of the data series ($R^2$=0.987). Each data point is the average of five replicates and the error bars are standard error of the mean.

Figure 10:
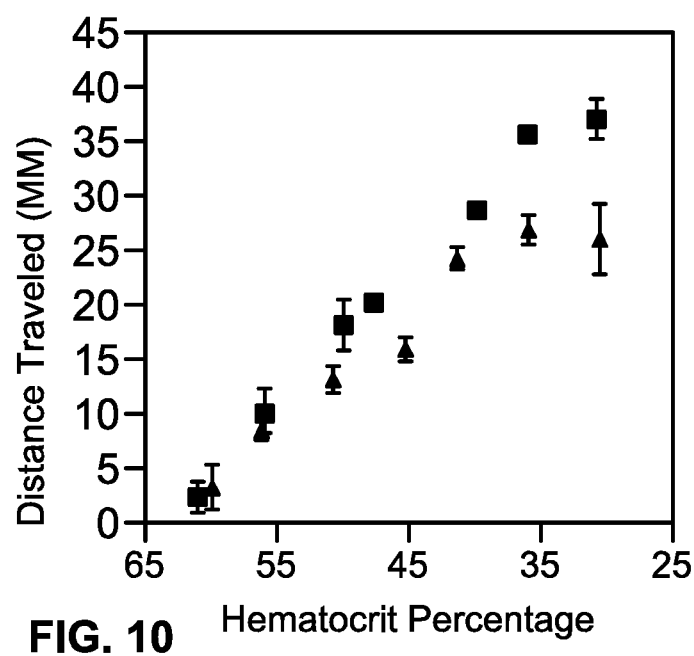
FIG. 10 is a graphical representation of various hematocrit percentages for samples of whole blood using microfluidic devices treated with sodium chloride with and without EDTA.

Referring to FIG. 10, the graphical representation shows various hematocrit percentages for samples of whole blood using microfluidic devices treated with sodium chloride with and without EDTA. The EDTA was treated on a lateral channel of the microfluidic device. Each data point for the EDTA-treated microfluidic-device data series is the average of three replicates and the error bars are standard error of the mean. Each data point for the data series of the microfluidic devices without EDTA treatment is the average of five replicates and the error bars are standard error of the mean.

Figure 11:
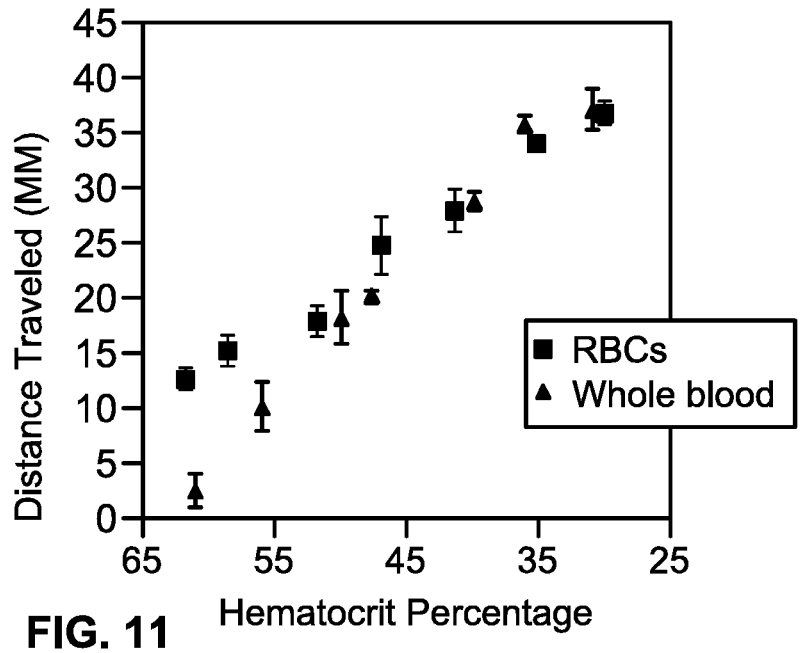
FIG. 11 is a graphical representation comparing differences in performance between isolated red blood cells ("RBCs") and whole blood.

Referring to FIG. 11, the graphical representation compares differences in performance between isolated RBCs and whole blood. Every data point for each data series is the average of five replicates and the error bars are standard error of the mean.

Figure 12:
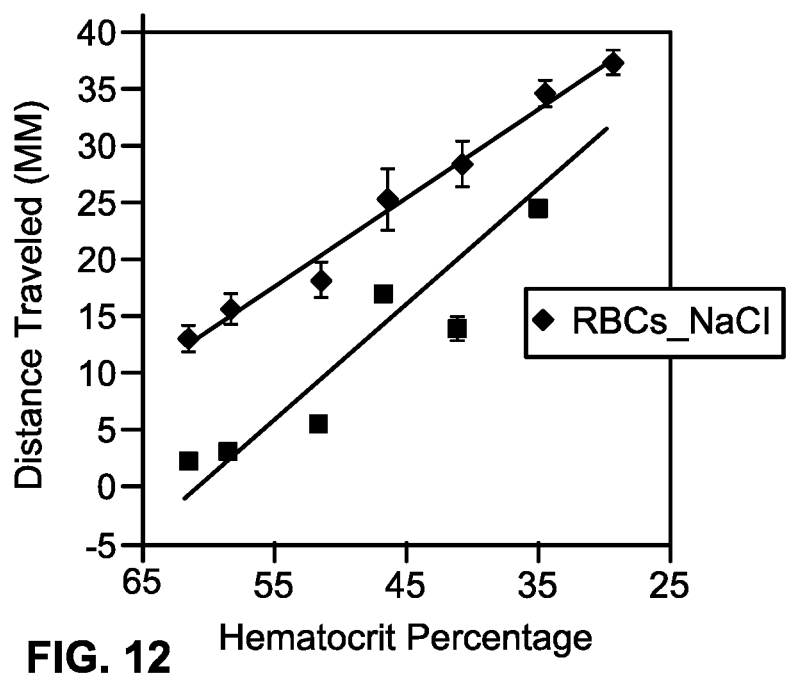
FIG. 12 is a graphical representation illustrating a comparison of performance of isolated RBCs on microfluidic devices that are treated and are not treated with sodium chloride.

Referring to FIG. 12, the graphical representation shows a comparison of performance of isolated RBCs on microfluidic devices that are treated and that are not treated with sodium chloride. Every data point for each data series is the average of five replicates and the error bars are standard error of the mean.

Figure 13A:
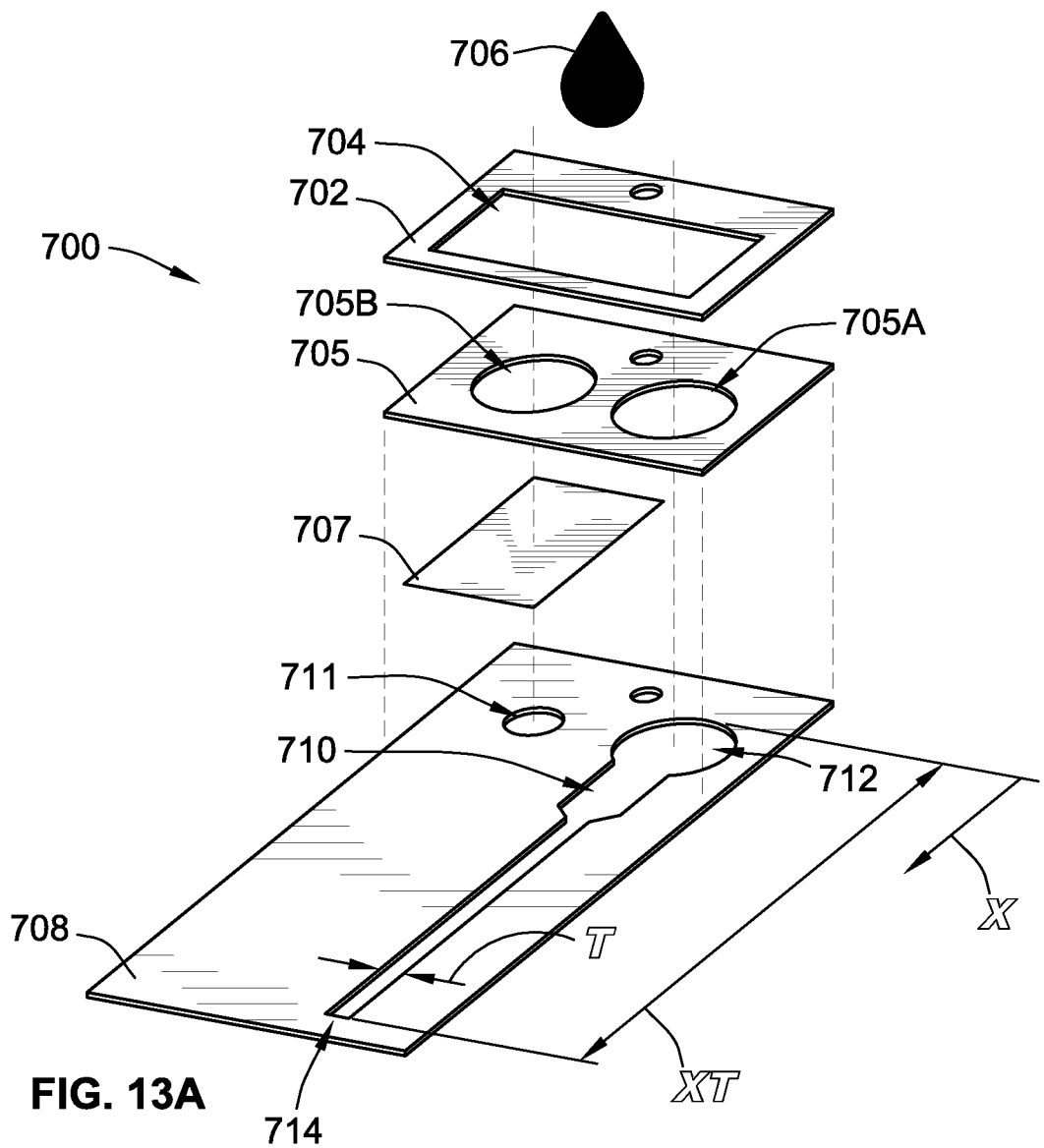
FIG. 13A is a perspective view illustration of a disassembled multi-layer microfluidic device.
Figure 13B:
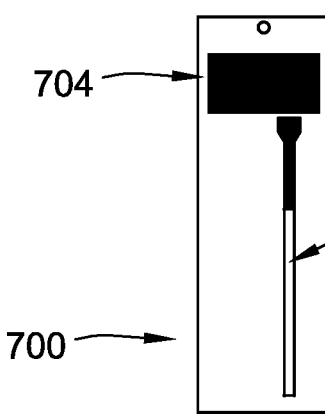
FIG. 13B is top view illustration of the microfluidic device of FIG. 13A shown in assembled form.
Figure 13C:
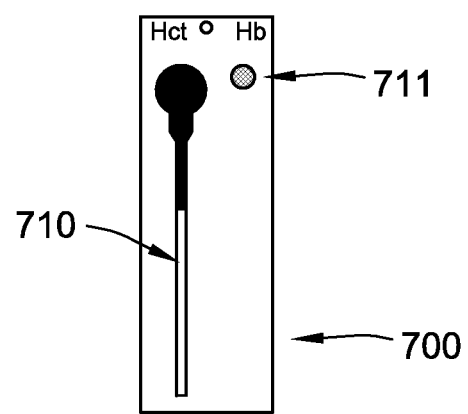
FIG. 13C is back view illustration of the microfluidic device of FIG. 13A shown in assembled form.

Referring generally to FIGS. 13A-13C, an alternative embodiment illustrates a microfluidic device 700 for simultaneously determining both a hematocrit amount and a hemoglobin amount from a liquid (e.g., blood) sample 706. Independently, hematocrit and hemoglobin measurements provide clinicians with important information about a patient's health status. The microfluidic device 700 is beneficial at least because these two values can be provided simultaneously at the bedside or at a point-of-care. The assay implemented by the microfluidic device 700 facilitates the use of paper in multi-step, autonomous analyses of blood. Accordingly, the microfluidic device 700 provides one example of simultaneous detection of multiple hematological indices and other soluble markers of health (e.g., creatinine and glucose) using inexpensive and disposable paper-based devices.

Referring specifically to FIG. 13A, the microfluidic device 700 includes a sample-addition layer 702 with a liquid-receiving area 704 through which the blood sample 706 is received into the microfluidic device 700. The sample-addition layer 702 is made from a porous material (e.g., paper) having a selected average pore size as described above in reference, for example, to the first layer of paper 102.

The microfluidic device 700 further includes a readout layer 708 that is stacked below, but not adjacent to, the sample-addition layer 702. The readout layer 708 is made from a porous material (e.g., paper) having a selected average pore size, for example, as described above in reference to the second layer of paper 108. The readout layer 708 includes a first channel 710 with a thickness T that has a starting end 712 positioned at least in part in an overlapping manner with the liquid-receiving area 704. The first channel 710 further has a terminating end 714 that extends laterally at a predetermined wicking distance XT from the starting end 712 in an X direction.

The readout layer 708 further has a second channel 711 that is adjacent to the first channel 710 and that is intended to receive a different type of cells from the liquid sample 706 than the type of cells received in the first channel 710. For example, the microfluidic device 700 is configured such that the first channel 710 indicates a hematocrit percentage in the liquid sample 706 and the second channel 711 indicates the hemoglobin level in the liquid sample 706. Although the second channel 711 is illustrated in FIG. 13A as a generally circular area, its shape and size can vary based on specific requirements. For example, according to an alternative embodiment, the second channel 711 is similar or identical in size and/or shape to the first channel 710.

The microfluidic device 700 further includes a sample-splitting layer 705 that is located between the sample-addition layer 702 and the readout layer 708. The sample-splitting layer 705 includes a first aperture area 705A through which at least some of the liquid sample 706 flows towards the first channel 710, and a second aperture area 705B through which at least some of the liquid sample 706 flows towards the second channel 711. According to an alternative embodiment, the aperture areas 705A, 705B are configured in the form of channels.

The microfluidic device 700 also includes a plasma separation membrane 707 that is located between the sample-splitting layer 705 and the readout layer 708. The membrane 707, according to this example, is configured with a size and shape that extends only between the second aperture area 705B of the sample-splitting layer 705 (which is above) and the second channel 711 of the readout layer 708 (which is below). In other words, the membrane 707 does not extend or act as a barrier between the first aperture area 705A of the sample-splitting layer 705 and the first channel 710 of the readout layer 708.

As such, according to one specific example, the membrane 707 filters cell debris from plasma remaining in the second aperture area 705B, to allow hemoglobin to be detected by a colorimetric reaction. Optionally, the pores of each of the sample-addition layer 702, the readout layer 708, the sample-splitting layer 705, and/or the membrane 707 are selected in accordance with the description provided above in reference to one or more of FIGS. 1A-12 (e.g., to cause a wicking effect through one or more of the first channel 710, the second channel 711, the first aperture 705A, and/or the second aperture 705B).

Referring specifically to FIGS. 13B and 13C, the microfluidic device 700 indicates a visual measurement based on the liquid sample 706. For example, a blood sample 706 is added to the microfluidic device 700 in the liquid-receiving area 704 where the blood sample 706 is allowed to saturate the sample-addition layer 702. The received blood sample 706 is split uniformly into the two aperture areas 705A, 705B. In the second aperture area 705B, a reagent (e.g., saponin) is stored to lyse all red blood cells. The plasma separation membrane 707 filters cell debris from the remaining plasma to allow hemoglobin to be detected by a colorimetric reaction (e.g., Drabkin's reagent stored on the microfluidic device 700).

The color formed by the colorimetric reaction is proportional to an amount of hemoglobin ("Hb"). For example, the reaction proceeds from a red color (indicative of low Hb) to a blue color (indicative of high Hb). As such, the reaction provides a visual readout of the level of Hb for a user.

The first aperture area 705A of the sample-splitting layer 705 is saturated with a fixed volume of blood, which allows the hematocrit ("Hct") assay to proceed in the first channel 710 of the readout layer 708. As previously discussed, the Hct assay requires the addition of a known volume of blood.

Figure 14C:
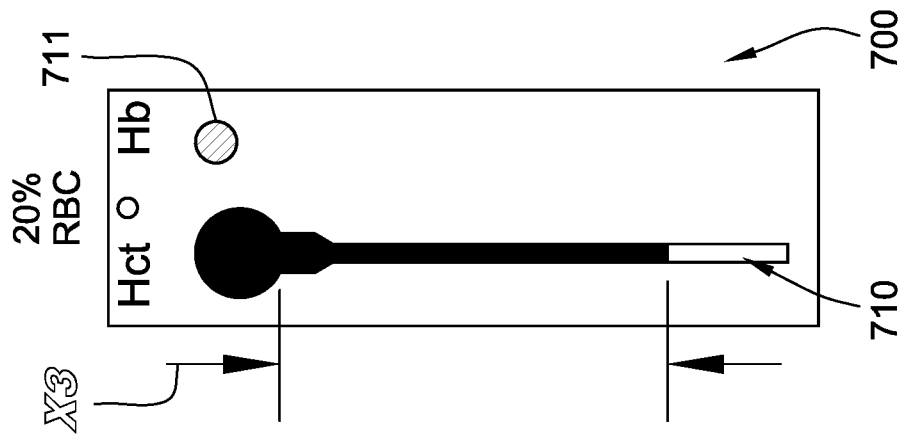
FIG. 14C illustrates the microfluidic device of FIG. 13A with a third visual readout of the Hct and Hb amounts.
Figure 14B:
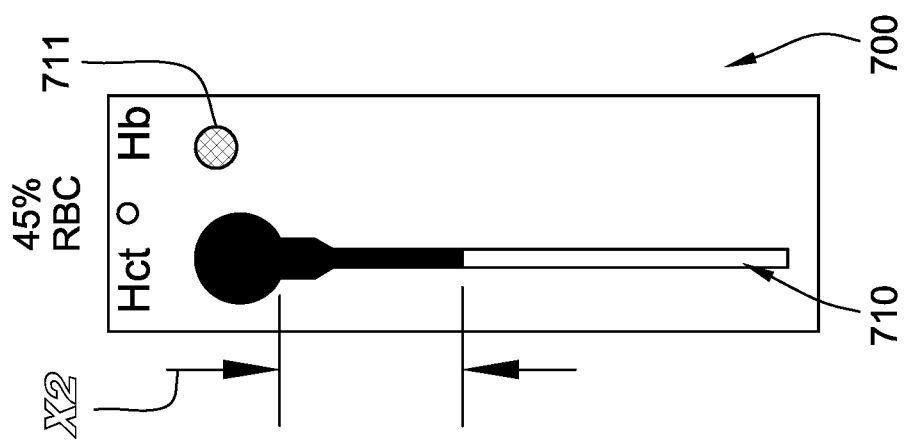
FIG. 14B illustrates the microfluidic device of FIG. 13A with a second visual readout of the Hct and Hb amounts.
Figure 14A:
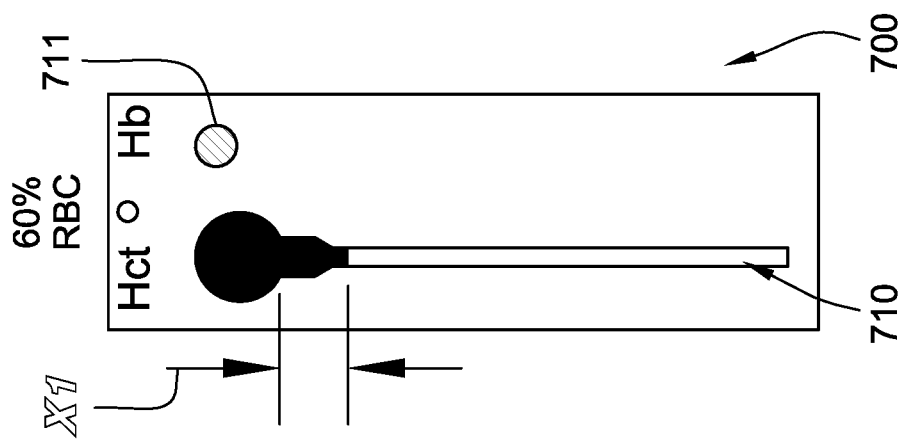
FIG. 14A illustrates the microfluidic device of FIG. 13A with a first visual readout of a hematocrit ("Hct") and hemoglobin ("Hb") amounts.

Referring to FIGS. 14A-14C, experimental data demonstrates that the amount detected Hb correlates with the measured hematocrit Hct. Specifically, samples of blood with red blood cells ("RBC") containing more cells at a higher Hct value have more hemoglobin Hb. For example, FIG. 14A shows that a relatively high 60% Hct value (as indicated by the traveled distance X1 in the first channel 710) correlates to a relatively high Hb amount (as indicated by a "blue" color in the second channel 711). FIG. 14B shows that a relatively medium 45% Hct value (as indicated by the traveled distance X2 in the first channel 710) correlates to a relatively medium Hb amount (as indicated by a changed color in the second channel 711). FIG. 14C shows that a relatively low 20% Hct value (as indicated by the traveled distance X3 in the first channel 710) correlates to a relatively low Hb amount (as indicated by a "red" color in the second channel 711).

According to alternative features of the microfluidic device described above, other markers for a multiplexed blood assay include one or more analytes of a blood metabolite panel. For example, the analytes include at least one of glucose, total protein, alkaline phosphatase, creatinine, and blood urea nitrogen (BUN).

Figure 15A:
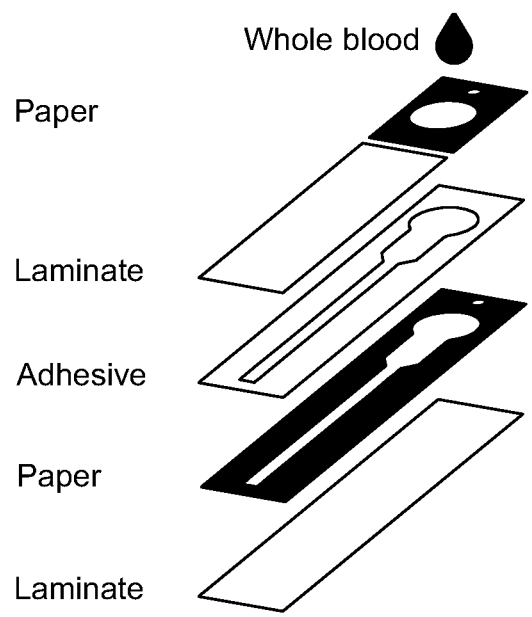
FIG. 15A is an illustration of a disassembled multilayer microfluidic device.
Figure 15B:
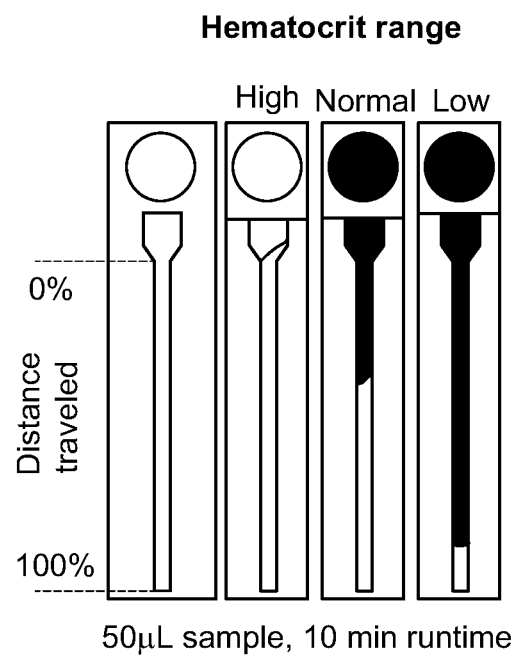
FIG. 15B illustrates the relationship between blood transport distance and hematocrit range in the multilayer microfluidic device of FIG. 15A and using an original device design with 50 microliters ("µL") of blood.
Figure 15C:
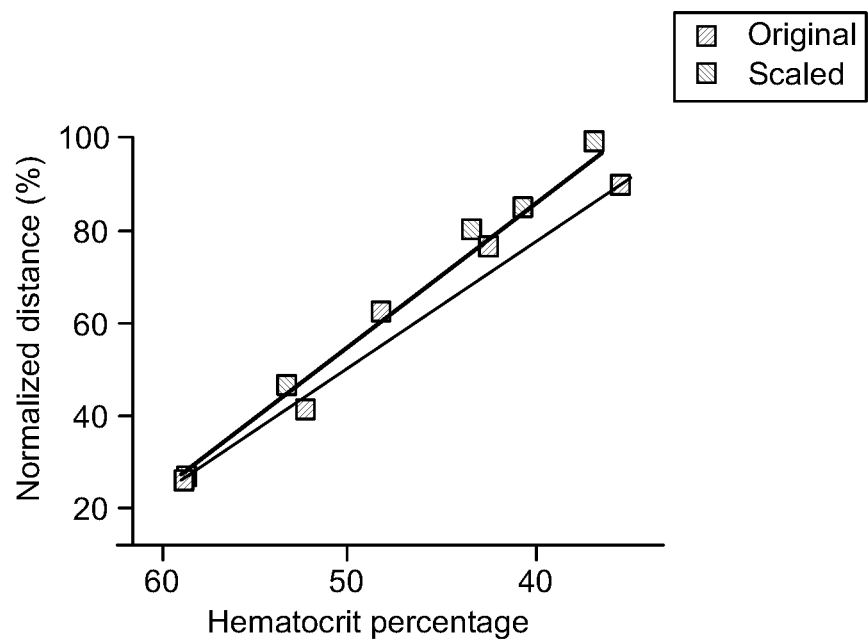
FIG. 15C illustrates data showing correlation between hematocrit percentage and normalized distance for original device designs using 50 µL of blood, as illustrated in FIG. 15B, and scaled device designs using only 10 µL of blood, as illustrated in FIG. 15D.
Figure 15D:
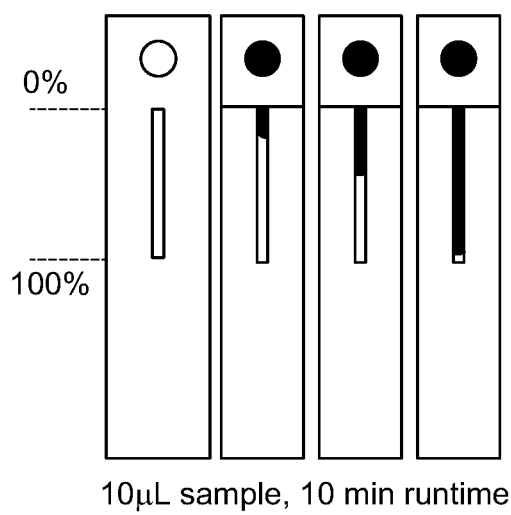
FIG. 15D illustrates a scaled device using only 10 µL of blood.

Referring to FIGS. 15A-15D, an exemplary embodiment of a multilayer microfluidic device is configured in accordance with principles described above. The multilayer microfluidic device has a paper-based hematocrit assay that is used to illustrate preliminary data in controlling transport of blood cells to measure Hct. The relationship between blood transport distance and hematocrit range is illustrated in FIG. 15B using an original device design with 50 microliters μL of blood. Data of FIG. 15C shows the correlation between hematocrit percentage and normalized distance for original device designs using 50 μL of blood, as illustrated in FIG. 15B, and scaled device designs using only 10 μL of blood, as illustrated in FIG. 15D. Although this example refers to paper, in other examples (using in addition or instead of those described above and below) include porous materials, e.g., meshes, membranes, or any other materials with pores and solid structures that define pores.

Figure 16A:
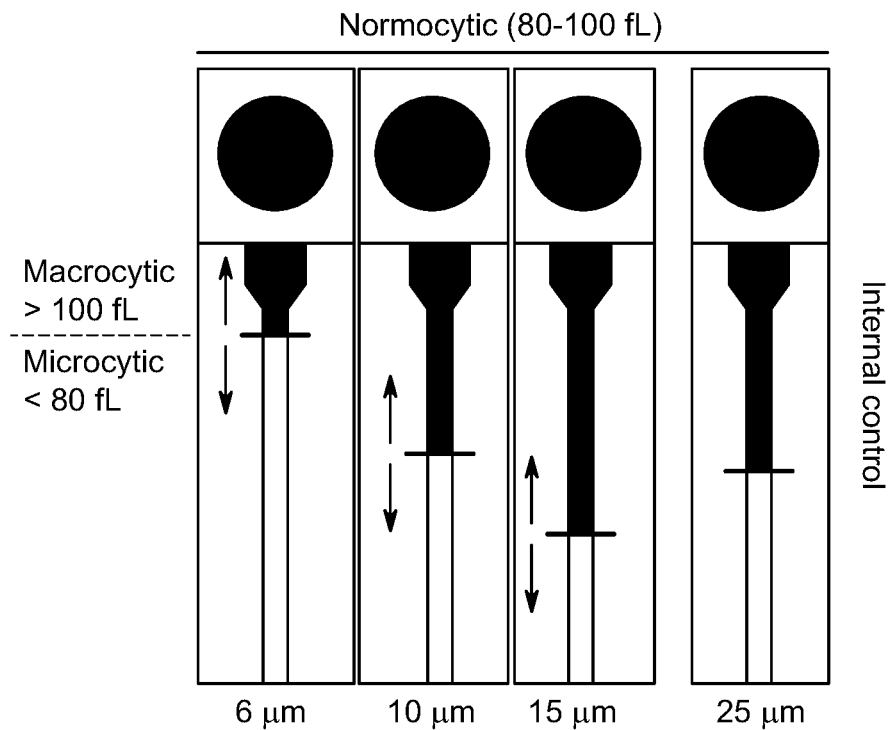
FIG. 16A is a schematic of a paper-based assay in which differential transport distances across multiple grades of paper are used to bin corpuscular volume ("MCV") as microcytic, normocytic, and macrocytic.
Figure 16B:
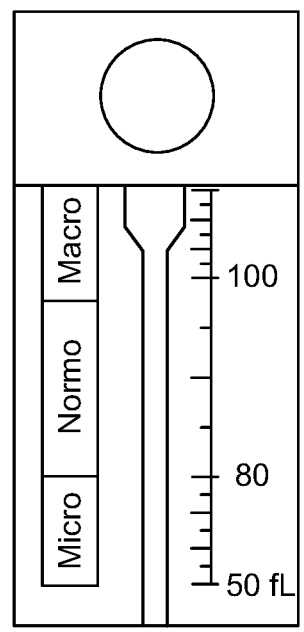
FIG. 16B is another schematic of a paper-based assay illustrating measurements of transport distance in a single grade of paper for quantifying the MCV.

Referring to FIGS. 16A and 16B, schematics show differential transport distances across multiple grades of paper that are used to bin MCVs as microcytic, normocytic, and macrocytic, and to measure transport distance in a single grade of paper that can be used to quantify the MCV. Papers with large average pore sizes, e.g., >25 μm, should not restrict the transport of RBCs of any size. Papers of intermediate pore size distinguish RBCs based on their MCV: (i) microcytic cells are transported farther than normocytic cells in papers with small pore sizes; and (ii) transport of macrocytic cells is reduced in comparison to normocytic cells (FIG. 16A). Additionally, a grade of paper is identified where transport distance is accurately related to the MCV (FIG. 16B).

Figure 17:
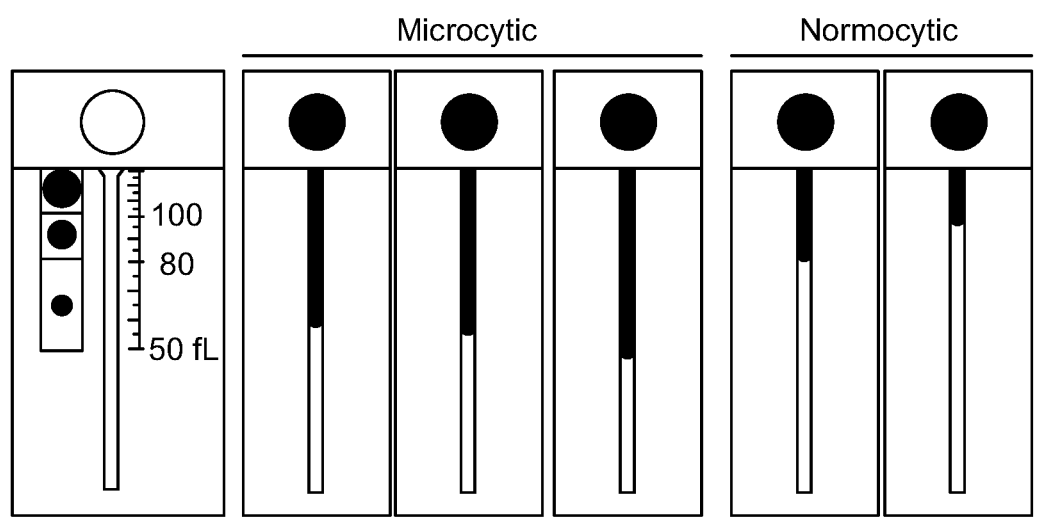
FIG. 17 illustrates paper-based devices for accurately placing MCVs into microcytic and normocytic bins based on transport distances.

Referring to FIG. 17, preliminary data of paper-based devices is intended to obtain accurate placement of MCVs into microcytic and normocytic bins based on transport distances. Specifically, the paper-based devices include five blinded samples of whole blood that are successfully differentiated and categorized based on transport distances in devices prepared from only a single grade of paper. A larger number of samples is desired to assess the accuracy of correlating transport distances to MCV.

Figure 18A:
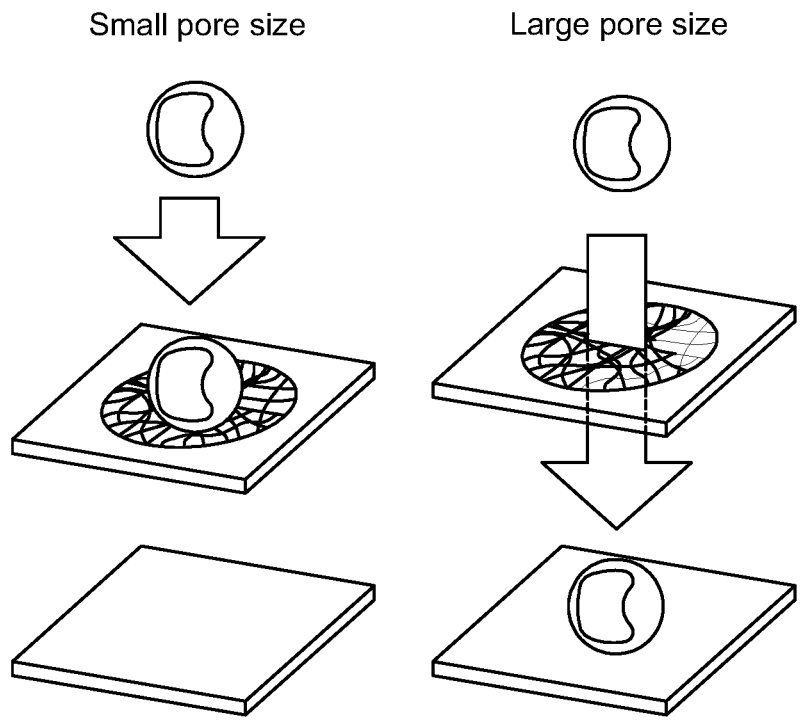
FIG. 18A is a schematic showing screening material strategy based on pore size.
Figure 18B:
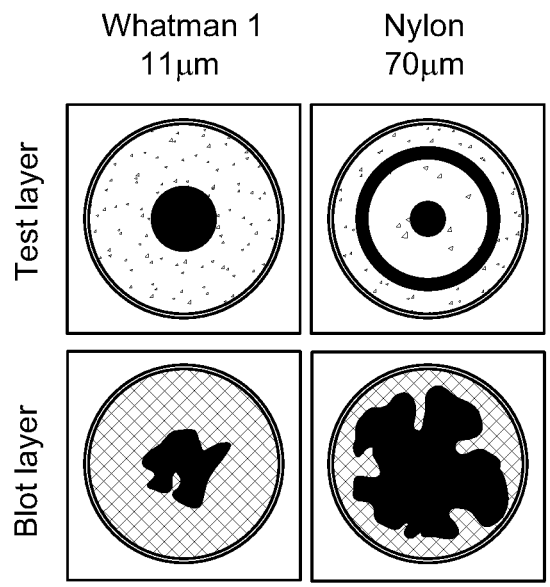
FIG. 18B shows scans of two-layer devices demonstrating that fluorescently stained CEM-CD4+T lymphocytes are largely retained by a test layer of chromatography paper (11 micrometers ("µm") pores) but nearly completely transported through a Nylon mesh (70 µm pores) onto a blot pad.

Referring to FIGS. 18A, 18B, and 19, previous observations from developing an Hct assay are applied to identify materials that permit WBC transport. To identify porous materials that meet the required criteria for every cell type of interest (e.g., larger neutrophils vs. smaller lymphocytes), the screen extends far beyond traditional chromatography papers and includes paper towels (e.g., Bounty Basic), synthetic wipers (e.g., TechniCloth), and porous meshes (e.g., for screen printing). The focus is on materials having pore sizes range from 10-100 μm and have porosities that range from 10-80%. The chemical properties of the material are also considered: leukocytes are negatively charged and a positively charged polymer mesh (e.g., Nylon) may lead to undesirable electrostatic capture. Chemical modification could provide control over such effects. These efforts parallel porometry and microCT analyses. A combination of material properties that, when matched to the size of each cell type, is expected to maximize the cell's cross-section and increase its probability of specific binding while minimizing non-specific capture by filtration.

The screen of materials using cultures of cells and primary cells isolated from whole blood is conducted as represented in FIG. 19. A simple two-layer device is prepared having a test material (to assess filtration) and a blot pad (to capture all transported cells). Cells are labeled with a general stain (e.g., Hoechst 33258 or DiO), which enable the visualization and quantitation of cells on each layer when imaged by microscopy, fluorescence imager, or scanner. Preliminary data demonstrates this experimental process comparing Whatman 1 chromatography paper (11 μm pore size, substantial filtration) and a Nylon mesh (70 μm pore size, negligible filtration) using CEM-CD4+T lymphocytes with diameters of approximately 11 μm (FIG. 18B).

Referring to FIGS. 20A-20C, a panel of reporters is conjugated to marker-specific antibodies in a strategy to create a paper-based cytometer. Options include enzymes (e.g., HRP), metabolic indicators (e.g., WST-8), colloidal particles (e.g., gold), and polymer photoinitiators. The resulting architecture is analogous to a sandwich immunoassay—the analyte of interest (i.e., a cell) is captured by an antibody immobilized on a solid support (e.g., paper) and detected using a paired antibody conjugated to a reporter. Based on the high copy numbers of surface markers, paired antibodies may recognize either identical or unique markers. Reporters are screened with dot-blot styled assays: (i) cells are labeled with antibody conjugates and unbound conjugate are washed away; (ii) labeled cells are spotted onto test zones in single-layer devices to retain all cells and evaluate maximum possible signal, and (iii) a substrate is added to visualize captured cells (FIG. 20C). This strategy enables the evaluation of two critical selection criteria: (i) generation of best visible signals with lowest limits of detection and greatest dynamic range and (ii) the direct comparison between calibration curves and the observed signals in fully assembled cytometers, which enable the quantitation of the number of captured cells.

Referring to FIGS. 21A-21D, a paper-based cytometer is designed to have multiple layers with a single patterned zone. Like all three-dimensional paper-based devices, each layer serves a unique function. For example, Layer 1 is for sample addition and potentially stores lysis reagents to process blood and eliminate RBCs. Layer 2 stores reporter species used to label and detect cells. Layer 3 is an optional layer that contains antibodies that bind off-target cells so that only desired cells are transported (i.e., negative selection). Layer 4 contains antibodies that bind targeted cells and complete the full sandwich immunocomplex required for detection (i.e., positive selection). These antibodies are immobilized by physiosorption or covalent attachment. Layer 5 collects all unbound cells and waste products. The selection of this material helps control assay duration via its wicking rate.

Figure 21A:
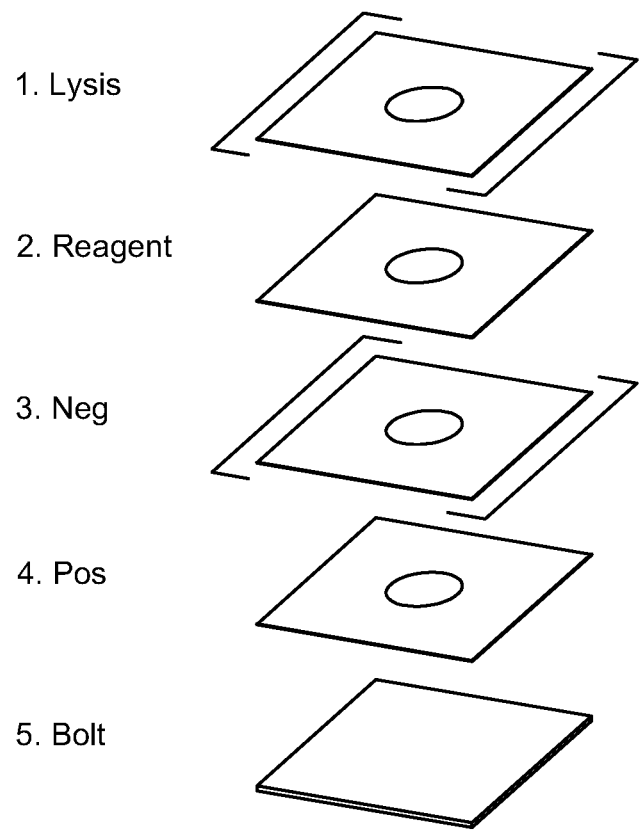
FIG. 21A illustrates devices that enable the sequential lysis of RBCs, labeling of WBCs, and negative and positive selection of desired populations by immobilized antibodies.
Figure 21B:
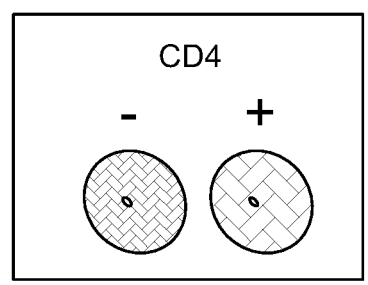
FIG. 21B illustrates preliminary data using WST-8 to visualize the specific capture and detection of CD4+T lymphocytes in only zones containing anti-CD4.

A singleplex cytometer requires only 10 μL of blood to perform a measurement. Briefly, the assay workflow is as follows: (i) blood is added to cytometers where RBCs are lysed and WBCs are labeled with reporters (this incubation step helps control assay duration); (ii) wash buffer is added to transport cells through negative and positive selection zones; (iii) unbound material is collected in the blot (the use of a wash buffer is commonplace in point-of-care diagnostics, e.g., OraQuick HIV tests); (iv) the device is delaminated to expose the capture layer (a peeling step effectively destroys the device, assists with disposal, and ensures that it is not reused); and (v) substrate is added, if necessary, to visualize and measure captured cells. Using this approach, paper-based cytometers immunophenotype cells for at least three markers (e.g., CD45+ reporter/CD20—negative selection/CD14+ capture for monocytes). This detection strategy with a cytometer specifically detects CD4+ T lymphocytes only in channels that contain immobilized anti-CD4 (FIG. 21B). Cell transport is completed in 5 minutes and color development using a metabolic indicator requires an additional 25 minutes.

Figure 21C:
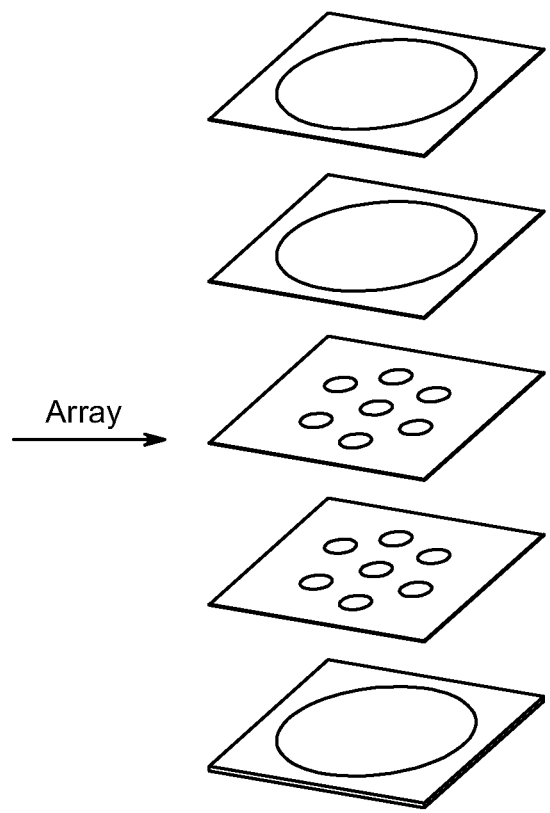
FIG. 21C illustrates arraying individual cytometers to create a device capable of performing multiple measurements simultaneously.

The analytical performance of paper-based cytometers is evaluated by creating calibration curves using known cell counts, determining limits of detection, and determining the dynamic range of the visible response. Assay conditions are tuned to ensure that each cell type is detectable across its range of clinically-relevant cell counts. Of particular interest is characterizing the specificity of cytometers for individual cell types when challenged with: (i) high counts of off-target cells (e.g., excess neutrophils for an eosinophil cytometer); (ii) complex mixtures of WBCs prepared from cultures or derived directly from the buffy coat of whole blood; and (iii) incomplete hemolysis. After individual cytometers are optimized, which includes identification of negative or positive selection methods, multiple cytometers are combined onto a common device (FIG. 21C). Based on previously determined device scaling rules and the results of singleplex cytometers, a multiplexed cytometer is expected to require approximately 75 μL of blood.

A large panel of clinical blood samples (N>100) is used to compare the performance of paper-based cytometers to standard hematology analyzers. This population provides insight into the effects that variations in any index (e.g., Hct) have on the accuracy of a measurement or diagnosis. To address these concerns, this cohort includes samples from patients with known presentations of complex conditions detectable by hematological (e.g., microcytic hypochromic anemia) or cytometric (e.g., neutropenia) assessment. Spike-and-recovery assays are used to determine the accuracy of the read guides (FIG. 21D), and the following are determined: (i) sensitivity and specificity, (ii) positive and negative predictive values, and (iii) receiver operating characteristic (ROC) curves.

Figure 21D:
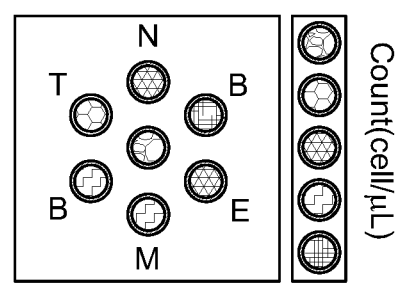
FIG. 21D illustrates disassembled devices to reveal capture zones for specific cell types.

Signals generated by paper-based cytometers are colorimetric and are intended to be interpreted by eye. Ideally, the operator compares the color of a test zone a read guide to determine cell counts in the applied sample (FIG. 21D). To obtain differentials, the operator either uses simple math or an additional guide (e.g., bin matching) to determine the ratio of the counts of each cell type to the total WBC count (i.e., differential analysis).

Figure 22A:
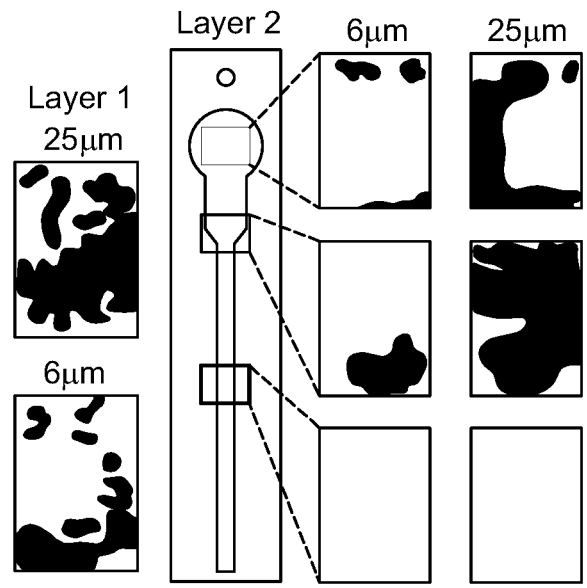
FIG. 22A illustrates controlled transport of mammalian cells in paper with WBCs filtered via a 6 µm pore layer while more WBCs are transported through 25 µm layer.
Figure 22B:
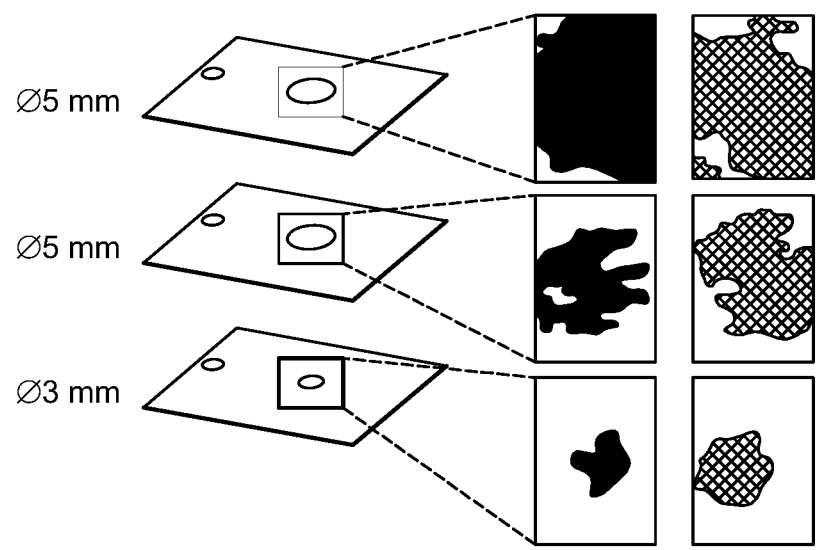
FIG. 22B illustrates transport of WBC improved in paper towels with large pore sizes (35 µm).

Referring to FIGS. 22A and 22B, a controlled transport of mammalian cells in paper is illustrated. For example, materials with larger pore sizes or higher porosities transport WBCs and ultimately enable the development of low-cost devices capable of detecting a brad class of cells from complex mixtures. According to the specific illustrated examples, mammalian cells are transported in paper with WBCs filtered via a 6 μm pore layer while more WBCs are transported through 25 μm layer (FIG. 22A). Transport of WBC is improved in paper towels with large pore sizes, e.g., 35 μm FIG. 22B).

Figures 23A, 23B:
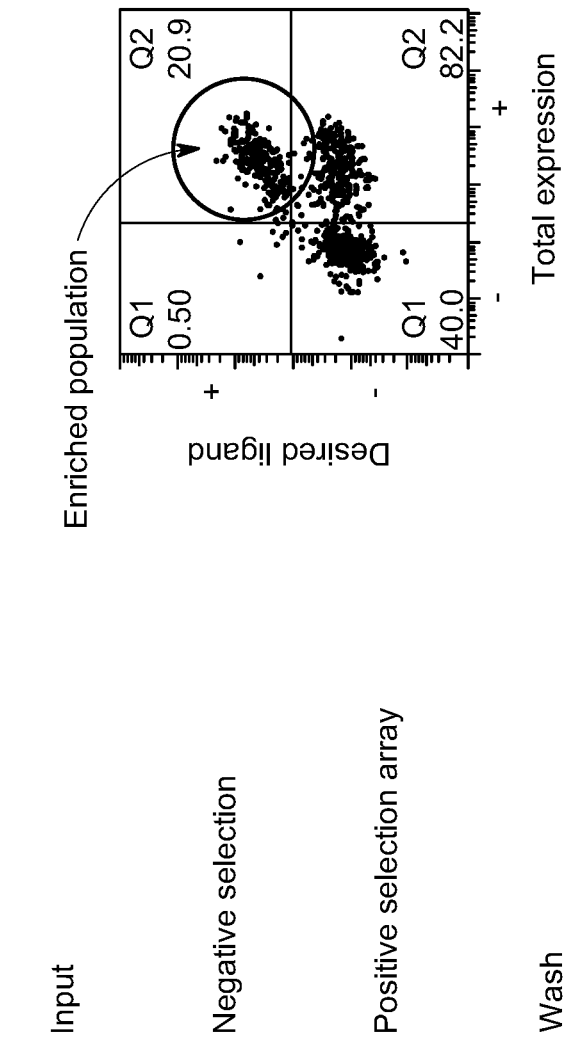
FIG. 23A is a schematic of a microfluidic device showing a paper-based cytometer for capturing and enriching yeast that binds a protein (MMP-9) that is impregnated in paper (positive selection array).
FIG. 23B is a plot showing the enriched population in the microfluidic device of FIG. 23A.

Referring to FIGS. 23A and 23B, enriched yeast in an experiment displays an antibody that binds matrix metalloproteinase 9 (MMP-9) from a solution where the majority of yeast does not display an MMP-9 binding protein. When a mixture of yeast is passed through paper that is impregnated with recombinant MMP-9 (FIG. 23A, positive selection), capture and specific enrichment of yeast is observed displaying the MMP-9 antibody (FIG. 23B). In contrast, no yeast is observed in paper lacking MMP-9 (FIG. 23A, negative selection). These findings demonstrate the ability to impregnate paper with a protein (MMP-9) and capture cells (yeast) with protein-embedded paper.

Figure 24A:
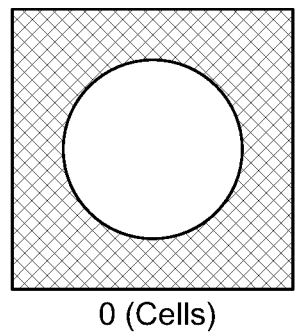
FIG. 24A shows a first image of a porous Nylon mesh with zero cells used to generate a calibration curve and to evaluate detection limits.
Figure 24B:
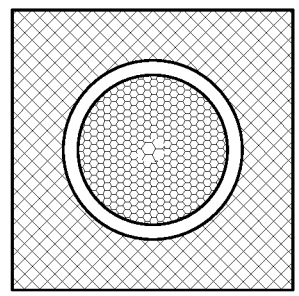
FIG. 24B shows a second image of the porous Nylon mesh of FIG. 24A with 500 cells.
Figure 24C:
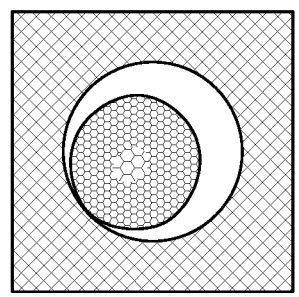
FIG. 24C shows a third image of the porous Nylon mesh of FIG. 24A with 1,000 cells.
Figure 24D:
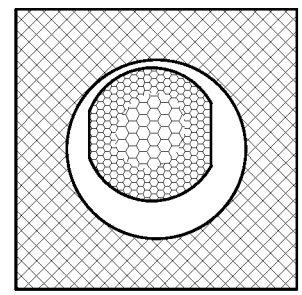
FIG. 24D shows a fourth image of the porous Nylon mesh of FIG. 24A with 2,000 cells.
Figure 24E:
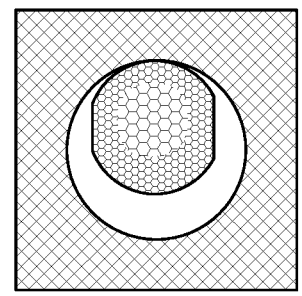
FIG. 24E shows a fifth image of the porous Nylon mesh of FIG. 24A with 3,000 cells.
Figure 24F:
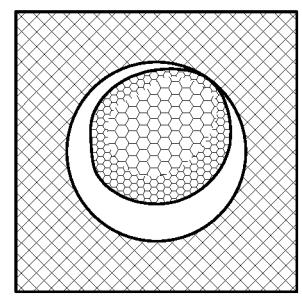
FIG. 24F shows a sixth image of the porous Nylon mesh of FIG. 24A with 4,000 cells.
Figure 24I:
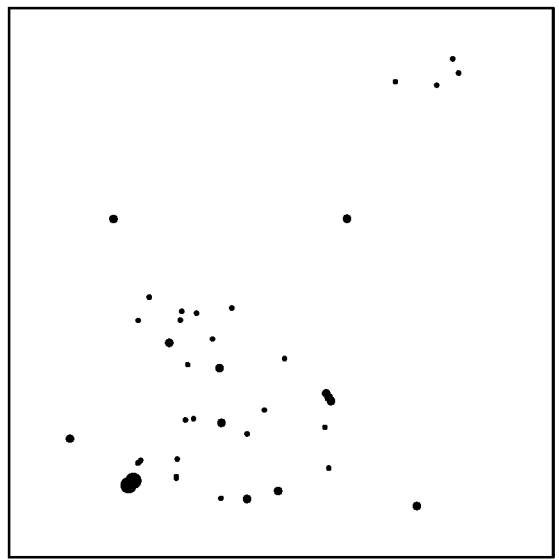
FIG. 24I shows a third image of selective capture of HER2-negative breast cancer cells (MDA-MB-231) with paper impregnated with HER2-binding protein 5F7.
Figure 24H:
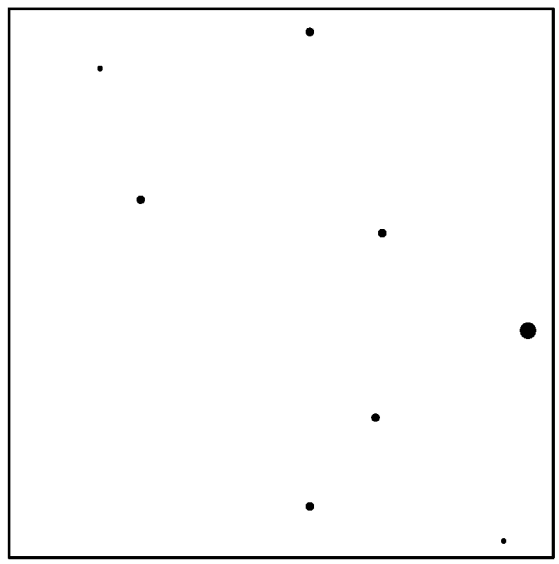
FIG. 24H shows a second image of selective capture of HER2-positive breast cancer cells (SK-BR-3) with no coating.
Figure 24G:
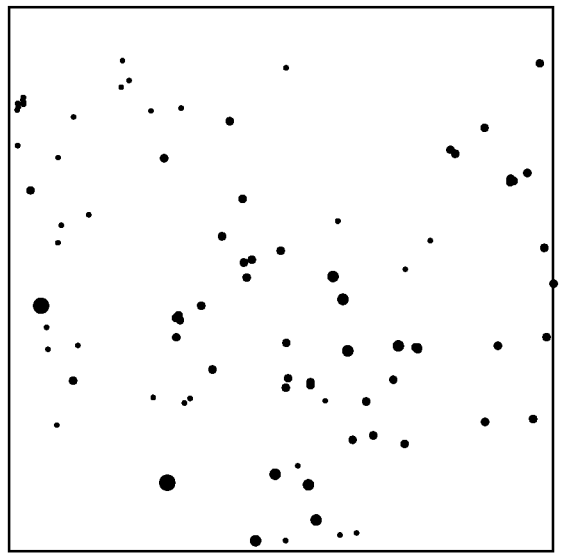
FIG. 24G shows a first image of selective capture of HER2-positive breast cancer cells (SK-BR-3) with paper impregnated with HER2-binding protein 5F7.

Referring to FIGS. 24A-24I, in a proof-of-capability study, HER2-binding nanobody, 5F7, is spotted onto Nylon capture membranes and physisorption is relied on as an immobilization strategy. It is determined that approximately 25% of the applied 5F7 protein is irreversibly absorbed into the Nylon mesh. Breast cancer cell capture is evaluated, across a range of concentrations, and 5F7-immobilized materials are created from porous Nylon to selectively capture HER2-positive SK-BR-3 breast cancer cells. Using samples containing cultured SK-BR-3 cells stained with a fluorescent dye and suspended in PBS buffer, a calibration curve is generated and detection limits are evaluated on porous Nylon meshes (FIGS. 24A-24F). Using fluorescent dyes as the reporter, as few as 500 total cells are observed captured by the device (FIG. 24B), although it is proposed that detection is significantly improved using reporter enzymes (e.g., luciferase) to amplify signal. Even so, a limit of detection in the range of hundreds to thousands of total cells is compatible with detecting sub-populations of cells found within a tumor biopsy. Critically, when cell-permeable Nylon is first impregnated with HER2-binding protein 5F7, HER2-positive SK-BR-3 cells treated with DiO (a commercially available membrane dye, FIG. 24G) are captured. In contrast, SK-BR-3 cells pass through Nylon that lack 5F7 (FIG. 24H), and far fewer numbers of HER2-negative MDA-MB-231 cells are captured in Nylon containing 5F7 (FIG. 24I).

Each of these embodiments and obvious variations thereof is contemplated as falling within the spirit and scope of the claimed invention, which is set forth in the following claims. Moreover, the present concepts expressly include any and all combinations and subcombinations of the preceding elements and aspects.

What is claimed is:

1. A microfluidic device, comprising:
   a sample-addition layer of a first porous material with pores having a first average pore size, the sample-addition layer having a liquid-receiving area through which a liquid sample is received into the microfluidic device;
   a sample-splitting layer located adjacent to the sample-addition layer, the sample-splitting layer having a first aperture for receiving a first portion of the liquid sample and a second aperture for receiving a second portion of the liquid sample;
   a separation membrane located adjacent to the second aperture of the sample-splitting layer, the separation membrane receiving only the second portion of the liquid sample from the second aperture; and
   a readout layer of a second porous material located adjacent the separation membrane, the second porous material having pores with a second average pore size that is different than the first average pore size, the readout layer having
      a first channel configured to receive in a starting end the first portion of the liquid sample from the sample-splitting layer, via the separation membrane, the first channel having a terminating end extending laterally at a predetermined wicking distance from the starting end, the first portion of the liquid sample flowing at least in part along the wicking distance to indicate a first value of the liquid sample, and
      a second channel being positioned adjacent to the first channel for receiving the second portion of the liquid sample, the second channel including a stored reagent that reacts with the second portion of the liquid sample to indicate a second value of the liquid sample.

2. The microfluidic device of claim 1, wherein the liquid sample is blood, the first value being indicative of a hematocrit percentage in the blood, the second value being indicative of a hemoglobin value in the blood.

3. The microfluidic device of claim 1, wherein the first portion and the second portion of the liquid sample are split uniformly between the first aperture and the second aperture of the sample-splitting layer.

4. The microfluidic device of claim 1, wherein the separation membrane is a third porous material with pores having a third average pore size that filters cell debris from the liquid sample.

5. The microfluidic device of claim 1, wherein at least one of the first porous material and the second porous material is a paper-based material.

6. The microfluidic device of claim 1, wherein the first value and the second value of the liquid sample are indicated simultaneously.

* * * * *